US011202698B2

(12) United States Patent
Hill et al.

(10) Patent No.: US 11,202,698 B2
(45) Date of Patent: Dec. 21, 2021

(54) TEXTURED SURFACES FOR IMPLANTS

(71) Applicant: Establishment Labs S.A., Alajuela (CR)

(72) Inventors: Ernie Hill, Manchester (GB); Ardeshir Bayat, Manchester (GB); Simon Barr, Manchester (GB)

(73) Assignee: Establishment Labs S.A., Alajuela (CR)

( * ) Notice: Subject to any disclaimer, the term of this patent is extended or adjusted under 35 U.S.C. 154(b) by 633 days.

(21) Appl. No.: 15/780,993

(22) PCT Filed: Dec. 2, 2016

(86) PCT No.: PCT/EP2016/079659
§ 371 (c)(1),
(2) Date: Jun. 1, 2018

(87) PCT Pub. No.: WO2017/093528
PCT Pub. Date: Jun. 8, 2017

(65) Prior Publication Data
US 2020/0268499 A1    Aug. 27, 2020

(30) Foreign Application Priority Data
Dec. 4, 2015  (GB) ...................................... 1521474

(51) Int. Cl.
*A61F 2/12* (2006.01)
*A61F 2/00* (2006.01)
(Continued)

(52) U.S. Cl.
CPC .............. *A61F 2/0077* (2013.01); *A61F 2/12* (2013.01); *A61L 27/34* (2013.01); *A61L 27/50* (2013.01);
(Continued)

(58) Field of Classification Search
CPC .......... A61F 2/12; A61F 2/0077; A61L 27/34; A61L 27/50
(Continued)

(56) References Cited

U.S. PATENT DOCUMENTS 3,761,047 A   9/1973  Mao
4,533,568 A   8/1985  McClinton et al.
(Continued)

FOREIGN PATENT DOCUMENTS

EP    0370292 A1    5/1990
EP    0850604 A2    7/1998
(Continued)

OTHER PUBLICATIONS

International Search Report for PCT/EP2016/079659 dated Apr. 20, 2017 (6 pages).
(Continued)

*Primary Examiner* — Suzette J Gherbi
(74) *Attorney, Agent, or Firm* — Bookoff McAndrews, PLLC

(57) ABSTRACT

An implant material having an implant surface comprising a plurality of tissue-contacting members arranged in a regular or irregular two-dimensional array, each tissue-contacting member having a convex curved tissue-contacting surface. Methods of preparing and using such implant materials.

19 Claims, 16 Drawing Sheets

(51) Int. Cl.
*A61L 27/34* (2006.01)
*A61L 27/50* (2006.01)

(52) U.S. Cl.
CPC .............. *A61F 2230/0013* (2013.01); *A61F 2230/0071* (2013.01); *A61F 2240/004* (2013.01); *A61F 2240/005* (2013.01); *A61L 2400/18* (2013.01); *A61L 2430/04* (2013.01)

(58) Field of Classification Search
USPC .................................................. 623/7–8
See application file for complete search history.

(56) References Cited

U.S. PATENT DOCUMENTS

| | | | |
|---|---|---|---|
| 5,158,571 A * | 10/1992 | Picha | A61F 2/12 606/192 |
| 5,961,552 A * | 10/1999 | Iversen | A61F 2/0077 623/8 |
| 8,986,377 B2 | 3/2015 | Richter et al. | |
| 9,700,415 B2 * | 7/2017 | Barrett | A61P 19/04 |
| 9,808,338 B2 | 11/2017 | Schuessler et al. | |
| 10,335,281 B2 * | 7/2019 | Barrett | A61F 2/30756 |
| 10,595,979 B2 * | 3/2020 | Bayat | A61F 2/0077 |
| 2002/0119177 A1 | 8/2002 | Bowman et al. | |
| 2004/0148024 A1 | 7/2004 | Williams | |
| 2004/0162613 A1 | 8/2004 | Roballey | |
| 2005/0216094 A1 | 9/2005 | Prewett | |
| 2006/0219143 A1 | 10/2006 | Brennan et al. | |
| 2008/0213611 A1 | 9/2008 | Asgari | |
| 2009/0088858 A1 | 4/2009 | Zinger et al. | |
| 2009/0118829 A1 * | 5/2009 | Powell | A61F 2/12 623/8 |
| 2010/0016989 A1 | 1/2010 | Lyngstadaas et al. | |
| 2010/0114303 A1 | 5/2010 | Su et al. | |
| 2010/0226943 A1 | 9/2010 | Brennan et al. | |
| 2011/0009960 A1 | 1/2011 | Altman | |
| 2011/0264213 A1 | 10/2011 | DeMiranda | |
| 2011/0276134 A1 | 11/2011 | Manesis et al. | |
| 2012/0046736 A1 | 2/2012 | Su et al. | |
| 2012/0116502 A1 | 5/2012 | Su et al. | |
| 2012/0165934 A1 | 6/2012 | Schuessler | |
| 2012/0267334 A1 | 10/2012 | Yamashita et al. | |
| 2012/0277860 A1 | 11/2012 | Dvir et al. | |
| 2013/0110243 A1 | 5/2013 | Patterson et al. | |
| 2013/0190699 A1 | 7/2013 | Stephan | |
| 2013/0190870 A1 | 7/2013 | Padsalgikar | |
| 2013/0021131 A1 | 8/2013 | Bommarito et al. | |
| 2014/0074237 A1 | 3/2014 | Yacoub et al. | |
| 2014/0257517 A1 | 9/2014 | Deichmann et al. | |
| 2017/0049549 A1 * | 2/2017 | Bayat | H01J 37/3056 |
| 2018/0200045 A1 | 7/2018 | Van Epps et al. | |
| 2019/0142574 A1 * | 5/2019 | Quiros | A61L 27/18 623/8 |
| 2019/0254803 A1 * | 8/2019 | Bluecher | A61F 2/0077 |
| 2019/0282353 A1 * | 9/2019 | Arzt | A61L 27/50 |
| 2019/0290382 A1 | 9/2019 | Martinez et al. | |
| 2020/0030124 A1 * | 1/2020 | Bluecher | A61L 31/14 |
| 2020/0100892 A1 * | 4/2020 | Limem | A61F 2/12 |
| 2020/0155292 A1 * | 5/2020 | Bluecher | A61L 27/50 |
| 2020/0170771 A1 * | 6/2020 | Bayat | A61F 2/12 |
| 2020/0188078 A1 * | 6/2020 | Bayat | A61F 2/0077 |

FOREIGN PATENT DOCUMENTS

| | | |
|---|---|---|
| JP | H0978102 A | 3/1997 |
| JP | H11240047 A | 9/1999 |
| WO | 9503752 A1 | 2/1995 |
| WO | WO 99/45860 | 9/1999 |
| WO | WO 00/21470 A1 | 4/2000 |
| WO | WO 2004/008983 A1 | 1/2004 |
| WO | WO 2007/051221 A1 | 5/2007 |
| WO | WO 2009/046425 A1 | 4/2009 |
| WO | WO 2011/097499 A1 | 8/2011 |
| WO | 2011127395 A1 | 10/2011 |
| WO | WO 2013/070290 A1 | 11/2011 |
| WO | 2013151755 A1 | 10/2013 |

OTHER PUBLICATIONS

Barnsley, G.P. et al., "Textured surface breast implants in the prevention of capsular contracture among breast augmentation patients: a meta-analysis of randomized controlled trials," *Plast. Reconstr. Surg.*, vol. 117, No. 7, pp. 2182-2190 (2006), abstract only.

Barr et al., "Current Implant Surface Technology: An Examination of Their Nanostructure and Their Influence on Fibroblast Alignment and Biocompatibility," *ePlasty*, vol. 9, p. 198-217 (2009).

Barr et al., "Patterning of Novel Breast Implant Surfaces by Enhancing Silicone biocompatibility, Using Biomimetric Topographies," *ePlasty*, vol. 10, pp. 246-268 (2010).

Barr, S. et al., "Breast implant surface development: perspectives on development and manufacture," *Aesthet. Surg. J.*, vol. 31, No. 1, pp. 56-67 (2011).

Barr, S. et al., "Development, Fabrication and Evaluation of a Novel Biomimetic Human Breast Tissue Derived Breast Implant Surface," *Acta Biomaterialia*, vol. 49, pp. 260-271 (2017).

Barr, S. et al., "Functional Biocompatibility Testing of Silicone Breast Implants and a Novel Classification System Based on Surface Roughness," *J. Mech. Behavior Biomed. Mater.*, vol. 75, pp. 75-81 (2017).

Castel, N. et al., "Polyurethane-coated breast implants revisited: a 30-year follow-up," *Arch. Plast. Surg.*, vol. 42, No. 2, pp. 186-193 (2015).

D'Andrea, F. et al., "Modification of cysteinyl leukotriene receptor expression in capsular contracture: Preliminary results," *Ann. Plast. Surg.*, vol. 58, No. 2, pp. 212-213 (2007), abstract only.

Davila et al., "Human Acellular Dermis versus Submuscular Tissue Expander Breast Reconstruction: A Multivariate Analysis of Short-Term Complications," *Archives of Plastic Surgery*, vol. 40, pp. 19-27 (2013).

Del Campo et al., "Fabrication Approaches for generating Complex Micro- and Nanopatterns on Polymeric Surfaces," *Chem. Rev.*, vol. 108, pp. 911-945 (2008).

Derby, B.M. et al., "Textured silicone breast implant use in primary augmentation: core data update and review," *Plast. Reconstr. Surg.*, vol. 135, No. 1, pp. 113-124 (2015).

Efanov, J.I. et al., "Breast-implant texturing associated with delamination of capsular layers: A histological analysis of the double capsule phenomenon," *Ann. Chir. Plast. Esthet.*, vol. 62, No. 3, pp. 196-201 (2017).

Ferret et al., "Clarification of Cereplas Breast Implant Manufacturing Processes," *Aesthetic Surgery Journal*, vol. 31, p. 725 (2011).

Flemming, R.G. et al., "Effects of synthetic micro- and nano-structured surfaces on cell behavior," Biomaterials, vol. 20, No. 6, pp. 573-588 (1999).

Gabriel, A. et al., "The Evolution of Breast Implants," *Clin. Plast. Surg.*, vol. 42, No. 4, pp. 399-404 (2015).

Garabédian, C. et al., "A Multi-Topographical-Instrument Analysis: The Breast Implant Texture Measurement," *Surf. Topogr.: Metrol. Prop.*, vol. 5, pp. 1-12 (2017).

Glicksman, C.A. et al., "A Step Forward Toward the Understanding of the Long-Term Pathogenesis of Double Capsule Formation in Macrotextured Implants: A Prospective Histological Analysis," *Aesthet. Surg. J.*, vol. 39, No. 11, pp. 1191-1199 (2018).

Harvey et al., "Designing Implant Surface Topography for Improved Biocompatibility," *Expert Rev. Med. Devices*, vol. 10, pp. 1-11 (2013).

Headon, H. et al., Capsular Contracture after Breast Augmentation: An Update for Clinical Practice, *Arch. Plast. Surg.*, vol. 42, No. 5, pp. 532-543 (2015).

"Implant Surfaces Analyzed," The University of Manchester, 2012 (approximate).

Kyle, D.J. et al., "Identification of molecular phenotypic descriptors of breast capsular contracture formation using informatics analysis

(56) References Cited

OTHER PUBLICATIONS of the whole genome transcriptome," *Wound Repair Regen.*, vol. 21, No. 5, pp. 762-769 (2013), abstract only.
Kyle, D. et al., "Development and Functional Evaluation of Biomimetic Silicone Surfaces with Hierarchical Micro/Nano-topographical Features Demonstrates Favourable in vitro Foreign Body Response of Breast-Derived Fibroblasts," *Biomaterials*, vol. 52, pp. 88-102 (2015).
Laboratoire national de métrologie et d'essais (LNE) Test Report, File L050836—Document DE/2, Dec. 8, 2010 (33 pages).
Laboratoire national de métrologie et d'essais (LNE) Test Report, File L050836—Document DE/3, Dec. 8, 2010 (33 pages).
Laboratoire national de métrologie et d'essais (LNE) Test Report, File L050836—Document DE/4, Dec. 8, 2010 (33 pages).
Liu et al., "Comparison of Outcomes Using AlloDerm Versus FlexHD for Implant-Based Breast Reconstruction," *Annals of Plastic Surgery*, pp. 105 (2013).
Maxwell, G.P. et al., "Benefits and Limitations of Macrotextured Breast Implants and Consensus Recommendations for Optimizing Their Effectiveness," *Aesthet. Surg. J.*, vol. 34, No. 6, pp. 876-881 (2014).
Mempin, M. et al., "The A, B and C's of Silicone Breast Implants: Anaplastic Large Cell Lymphoma, Biofilm and Capsular Contracture," *Materials*, vol. 11, pp. 1-11. doi:10.3390/ma11122393 (2018).
Mendonca, G. et al., "Advancing dental implant surface technology—from micron—to nanotopography," Biomaterials, vol. 29, No. 28, pp. 3822-3835 (2008), abstract only.
Militky et al., "Surface Roughness and Fractal Dimension," *The Journal of the Textile Institute*, vol. 92, pp. 91-113 (2001).
Munhoz, A.M. et al., "Nanotechnology, nanosurfaces, and silicone gel breast implants: current aspects," *Case Reports Plast. Surg. Hand Surg.*, vol. 4, No. 1, pp. 99-113 (2017).
Rompen, E. et al., "The effect of material characteristics, of surface topography and of implant components and connections on soft tissue integration: a literature review," *Clin. Oral Implants Res.*, vol. 17, Suppl. 2, pp. 55-67 (2006).
Salzberg et al., "Immediate Breast Reconstruction Using Porcine Acellular Dermal Matrix (Strattice™): Long-term Outcomes and Complications," *Journal of Plastic, Reconstructive & Aesthetic Surgery*, vol. 66, pp. 323-328 (2013).
Schulte, V.A. et al., "Surface topography induces fibroblast adhesion on intrinsically nonadhesive poly(ethylene glycol) substrates," *Biomacromolecules*, vol. 10, No. 10, pp. 2795-2801 (2009), abstract only.
Seth et al., "A Comparative Analysis of Cryopreserved Versus Prehydrated Human Acellular Dermal Matrices in Tissue Expander Breast Reconstruction," *Annals of Plastic Surgery*, vol. 70, pp. 632-635 (2013).
Sforza, M. et al., "A Preliminary Assessment of the Predictability of Fat Grafting to Correct Silicone Breast Implant-Related Complications," *Aesthetic Surgery Journal*, vol. 36, pp. 886-894 (2016).
Sforza, M. et al., "The $21^{st}$ Century Silicone Breast Implant," *J. Surg. Open Access*, vol. 2, pp. 1-2 (2016).
Sforza, M. et al., "Preliminary 3-Year Evaluation of Experience With SilkSurface and VelvetSurface Motive Silicone Breast Implants: A Single-Center Experience With 5813 Consecutive Breast Augmentation Cases," *Aesthetic Surgery Journal*, vol. 38, pp. 562-573 (2018).
Shih, B. et al. "Identification of novel keloid biomarkers through profiling of tissue biopsies versus cell cultures in keloid margin specimens compared to adjacent normal skin," *Eplasty*, vol. 10, pp. 187-202 (2010).
Shih, B. et al., "Comparative genomic hybridisation analysis of keloid tissue in Caucasians suggests possible involvement of HLA-DRB5 in disease pathogenesis," *Arch. Dermatol. Res.*, vol. 304, No. 3, pp. 241-249 (2012), abstract only.
Stevens, W.G. et al., "Risk factor analysis for capsular contracture: a 5-year Sientra study analysis using round, smooth, and textured implants for breast augmentation," *Plast. Reconstr. Surg.*, vol. 132, No. 5, pp. 1115-1123 (2013).
Syed, F. et al., "Fibroblasts from the growing margin of keloid scars produce higher levels of collagen I and III compared with intralesional and extralesional sites: clinical implications for lesional site-directed therapy," *Br. J. Dermatol.*, vol. 164, No. 1, pp. 83-96 (2011), abstract only.
Tan, K.T. et al., "Tumour necrosis factor-$\alpha$ expression is associated with increased severity of periprosthetic breast capsular contracture," *Eur. Surg. Res.* vol. 45, Nos. 3-4, pp. 327-332 (2010), abstract only.
Tan et al., "Hyaluronan, TSG-6, and Inter-$\alpha$-Inhibitor in Periprosthetic Breast Capsules: Reduced Levels of Free Hyaluronan and TSG-6 Expression in Contracted Capsules," *Aesthetic Surgery Journal*, vol. 31, pp. 47-55 (2011).
Valencia-Lazcano et al., "Characterization of Breast Implant Surfaces and Correlation with Fibroblast Adhesion," Journal of the Mechanical Behavior of Biomedical Materials, vol. 21, pp. 133-148 (2013).

\* cited by examiner

TEXTURED SURFACES FOR IMPLANTS

CROSS-REFERENCE TO RELATED APPLICATIONS

This application is the U.S. national phase entry under 35 U.S.C. § 371 of International Application No. PCT/EP2016/079659, filed on Dec. 2, 2016, which claims benefit to GB Application No. 1521474.5, filed on Dec. 4, 2015.

TECHNICAL FIELD

This invention relates to biocompatible implant materials having textured surface topographies for reducing an undesirable cellular response upon implantation into the body and subsequent capsular contracture formation, with particular application to prosthetic implants, such as silicone breast implants. Methods for preparing such surfaces, and templates useful for preparing such surfaces are also disclosed.

BACKGROUND

Implant based surgery is performed in a variety of settings, from reconstruction for congenital anomalies and post mastectomy defects for oncological reasons, to augmentations for cosmetic reasons. Unfortunately, currently available breast implants are not without their innate complications. The most common complication and cause for patient dissatisfaction post implantation is capsular contracture formation.(1) 1,773,584 breast augmentations for aesthetic reasons were declared worldwide to the International Society of Aesthetic Plastic Surgery in 2014.(2) Capsular contracture rates have been speculated to occur in as many as 17.5% of implant based procedures, and therefore a significant number of these women will have experienced capsular contracture.(3)

Capsular contracture is the exaggeration of foreign body response of the patient's breast tissue to the breast implant. The normal sequence of the foreign body reaction to a biomaterial results in a capsule which walls off the implant. (4) However, in some patients this response is exaggerated and the fibrous capsule becomes thickened, fibrotic and less pliable which can manifest as mastalgia, breast firmness and a poor aesthetic result. As a consequence many patients will require reoperation to decompress capsular contracture.(5)

Capsular contracture has been shown to be multifactorial, with filler material, sub-muscular placement of the implant, adjuvant radiotherapy, bacterial colonisation of the implant and implant surface texture all being implicated in its development.(6)

Current breast implants, with an elastomer shell and saline or silicone gel filler evolved from a design theorised in the 1960's, which evolved into a textured, polyurethane coated implant in the late 1960's.(7, 8) As a consequence of concern that polyurethane was pro-cancerous and because of the ability of polyurethane foam to reduce contracture rate, due to a belief that implant texturing reduced contracture rates, several implant surface textures made from silicone were developed(9, 10). Since then the basic shell and filler construction has endured but with subtle modifications to the texture on the surface of these implants. The textures which are currently available are made either by imprinting salt or polyurethane foam into the surface of these implant shells or by moulding the implant shell from a pre-textured mould. (11) Whilst the manufacturing techniques employed are crude, a systematic review and a meta-analysis, have both demonstrated the protective effect of implant texture on capsular contracture.(12, 13) However, no study has demonstrated that one particular implant surface is most efficient at reducing contracture and the predominant approach of implant companies to date has been to market their implants with little scientific evidence to attest to their ability.

Micro and nano surface topographies have been shown to influence cell proliferation, attachment, adhesion, migration and morphology.(14) Many of the morphological topographies which exist in vivo which interact with cells are those from the extra cellular matrix (ECM) and it has been shown that the ECM of different tissue types promote the production of tissue morphologies from where they are derived.(15, 16) Implant textures have also been theorised to reduce contracture by disrupting the planar capsule which surrounds the implant and promoting the ingrowth of breast tissue.(17) However, deep "macro-textures", with deep surface features have also been shown to shed particulate silicone and increase the inflammation within implant capsules.(18)

In general, implant surfaces may have a primary surface profile made up of the surface form, which is the general shape of the material surface. For instance, the surface of a breast implant will generally adopt a curved form, perhaps with additional contours/waves which may be natural features/undulations that form as a result of the physical make-up of the implant. The way in which such surfaces interact with body tissue at a cellular level is however better described by reference to the surface roughness, which refers to the topographical texture of the primary implant surface on a smaller scale.

Breast implants are typically formed by dipping an implant-shaped template (mandrel) into liquid polymer so that it becomes uniformly coated. Prior to curing, the implant can be subjected to a texturizing process such as imprinting on a mould to create a patterned texture in silicone (e.g. Mentor Siltex™ Implant). The mandrel is then placed in a hot, laminar flow cabinet to allow for the polymer to solidify around the template (curing). This curing step allows for an equal amount of heat to be applied around the implant so that a homogenous surface is created. This process can be repeated several times to increase the thickness of the implant and the implant may then be further treated with a solvent if it is to be smooth (to further smooth out the surface). Silicone breast implants are thus typically made through this same basic process, regardless of whether they are designed to be smooth or textured.

In this regard, implant surfaces that are "smooth" do in fact usually exhibit an unintentional minor degree of surface roughness as a result of fine ripples, grooves and/or other surface anomalies that are an inherent bi-product of the process by which the surfaces are prepared (for instance forming during the curing process as the liquid silicone trickles down the mandrel under force of gravity).

Formally "textured" surfaces, however, typically comprise a heavily textured surface topography. Such textures may be regular repeating geometric patterns or may be irregular in nature.

WO2009/046425 for example describes textured implant surfaces having a highly ordered regular geometric repeating pattern (parallel bars) at the micro- or nano-scale which are claimed to disrupt bacterial biofilm formation on the implant surface. The repeating pattern is formed by production of a master pattern using photolithographic techniques as applied in semiconductor manufacture and the master pattern is then used to contact print replicated patterns on the surface of the implant. However, whilst conventional photolithographic techniques can provide simple geometric structures such as the grooves depicted in WO2009/046425, such methods are not attractive when more complex geometric patterns are sought because such patterns depend on the preparation and use of photo-masks with graded levels of opacity through which graded levels of UV light may pass onto the photo-resist. Such photo-masks are expensive to produce and cannot be altered once produced, meaning that each desired design/pattern requires the prior preparation of bespoke photo-masks.

WO95/03752 (see FIG. 4) also depicts an implant surface having a highly ordered regular geometric repeating pattern (pillars). These uniform micro-textured surfaces may be produced by use of ion-beam thruster technology (see e.g. page 2 of WO95/03752). However, such uniformly patterned implant surfaces typically lead to the orientation of fibroblasts in conformity with the respective surface pattern (see e.g. paragraphs 28, 34 and FIGS. 14 and 15 of WO2009/046425). As explained above, however, the organised orientation of fibroblasts and, subsequently, collagen is understood to be a key stage in the promotion of fibrotic capsule contracture. Thus, while such ordering of fibroblast might be more acceptable in external applications such as for use in wound healing, such highly ordered patterned surfaces are not therefore ideal for use in prosthetic implants, such as breast implants, which are prone to capsule formation and contracture.

A variety of irregular (i.e. non-uniform) textured implant surfaces have however been proposed in the literature with a range of different cellular outcomes observed. A number of approaches to providing textured surfaces have however failed to reduce or prevent capsule formation and subsequent contracture. For instance, paragraphs 86-89 and FIGS. 7 to 9 of WO 2011/097499 describe a number of irregular textured surfaces, which fail to provide desirable capsule modulation. A 'salt loss' technique is used in the production of commercially available Biocell™ (Allergan, Inc.). Such surfaces are described and illustrated in more detail in [Barr, S. 2009]. This technique results in an open-cell structure. Implant surfaces formed by this "salt loss" technique are also depicted in FIG. 5 of WO95/03752. Such implants are not however ideal as introduction of foreign particles to the silicone surface may lead to detrimental effects on the silicone implant properties, for instance if the relevant salts become encapsulated in the silicone.

An alternative technique for forming an open-cell structure involves the use of an open cell foam or fibrous polymeric fabric to either form or imprint a pattern on the implant surface. For instance, the commercially available Siltex™ implant (Mentor), uses a mandrel with a polyurethane foam texture that is imprinted into the silicone during curing. Similar fabric/open cell foam-based texturizing techniques are also described in US 2011/0276134, WO 2011/097499 and US2002/0119177. If such open cell-like structures are achieved using a fabric with a uniform geometry, then open-cell structures with small-scale irregularity but long-distance uniformity may be achieved (see e.g. FIGS. 10 and 12 of US 2011/0276134). Whilst such open cell structures are reported to achieve some success in preventing capsule formation, they also have drawbacks because the fine interstices and edges formed as a result of the process may lack robustness and may break away from the implant surface under frictional forces leading to detached silicone fragments in the body. Furthermore, the large, typically macroscopic, pores formed by such processes have deep sides and pits which means that cells become embedded in the deep valleys of the implant and cannot migrate due to sides that are too steep for the cells to climb. Whilst this may hinder the process of capsule formation, the cells cannot display natural migratory and proliferative behaviour with contact inhibition of cells within deep troughs of heavily textured implants. This is undesirable since an adherent cell such as a fibroblast that is able to attach, migrate, proliferate and function on a surface with minimal stress and without inhibition, is likely to behave as a fibroblast would in vivo within native ECM. Nonetheless, the deep troughs typically still allow the eventual substantial in-growth of cells into the surface pores, but whilst this may firmly anchor the implant in place in the body, excessive tissue in-growth may lead to difficulties later if the implant has to be removed or replaced (for instance if capsular contraction nonetheless occurs) as a large amount of body tissue will also have to be cut away with the implant.

WO95/03752 discloses an alternative method for producing irregular surface topographies in silicone breast implants by adding filtered silicone particles to the still tacky surface of the mandrel before curing and application of a top-coat (pages 10 to 12).

WO2015/121686, having inventors in common with the present application, proposes an irregular textured surface modelled on the basement membrane of the skin, the specific characteristics of the basement membrane being such as to impart the synthetic surface with corresponding characteristic values for mean surface roughness Sa, root mean square height Sq, maximum peak height to trough depth Sz, mean surface skewness Ssk, mean excess kurtosis value (Sku minus 3), and fractal dimension.

SUMMARY OF INVENTION

The inventors propose new biomimetic textured surface topographies for implants, particularly breast implants. The inventors have found in particular that by controlling aspects of the surface texture to resemble corresponding features of the surface topography of adipose tissue improved cellular response, indicative of reduced capsular contraction, and appropriate cellular anchoring/in-growth could be achieved.

The inventors sought to produce an implant topography with a provenance from the breast, specifically adipose tissue from the breast. The inventors have employed site-specific biomimicry to generate a novel implant surface that is adapted to its intended implant site. Thus, when an implant comprising the novel implant surface is implanted, as is conventional, into the tissue plane between the adipose tissue of the breast anteriorly and the pectoralis muscle fascia posteriorly, the surface abutting the adipose tissue provides an effective environment for cell adhesion, growth and proliferation.

In order to arrive at the novel implant surface, the inventors isolated adipose tissue from the adipose tissue interface, conducted a series of fixation techniques, characterised it using imaging techniques, modelled it with bespoke image analysis, and generated a synthetic replica of the observed adipose tissue surface using 3D photolithography.

In a first aspect the present invention provides an implant material having an implant surface, which implant surface comprises a plurality of tissue-contacting members arranged in a regular or irregular two-dimensional array, each tissue-contacting member having a convex curved tissue-contacting surface.

DETAILED DESCRIPTION OF THE INVENTION

Surface Texture

The inventors have identified characteristics of adipose tissue surface that, when reproduced on the surface of an implant, may contribute to improved cell response and reduced capsular contracture. In particular, one or more of the following surface features can be reproduced on the implant surface: the approximately hemispherical form of the adipose cells that form the surface of the adipose tissue (against which the implant will be placed); the close packing of the adipose cells on the surface (which close packing effectively truncates the hemispheres, causing them to appear to fuse together); the density of cells (cells per unit area), that being related to the close packing; the average size (diameter) of the adipose cells (in turn dictating the radius of curvature that the cells present at the surface); the distribution or variance in size (diameter); the average spacing between adjacent cells (nearest neighbour distance); the distribution or variance in spacing between adjacent cells (nearest neighbour distance); the surface coverage of the cells (extent to which the tissue surface is formed from things other than the cells); and the height range for the nano-texture on the cell surface (the nano-variation of height overlaid on the micro/macro topography of the close packed approximately hemispherical adipose cells).

Without wishing to be bound by theory, the provision of an adipose tissue-like surface on the implant may permit the implant to tessellate with or pack into the adipose tissue of the breast. The biomimetic topography suitably provides an environment for cells that is less likely than conventional implant surfaces to cause foreign body response and especially capsular contracture.

The implant surface of the implant material of the invention seeks to mimic one or more of the characteristics of the adipose tissue surface that has been carefully characterised by the inventors.

The tissue-contacting members of the implant surface correspond to the adipose cells that provide the adipose surface topography. As noted above, a characteristic of the adipose tissue surface is the array of approximately (part) hemispherical shapes—a globular form, and so the tissue-contacting members of the implant surface have a convex (that is, extending outwardly/away from the surface) curved tissue-contacting surface. The provision of an array of such convex curved surfaces mimics the multiple curved surfaces arising from the close packing of the adipose cells.

Suitably the convex curved tissue-contacting surface has a radius of curvature for which the radius is approximately constant. That is, the curvature is approximately spherical curvature. Suitably the convex curved tissue-contacting surface corresponds to a portion of the surface of a sphere. Suitably the convex curved tissue-contacting surface corresponds to a substantial part of the (curved) surface of a hemisphere.

Suitably each tissue-contacting member has the shape of part of or all of a hemisphere.

Suitably each tissue-contacting member, or at least its convex curved tissue-contacting surface has a globular shape. The tissue-contacting members suitably have the shape of part or all of a globe. That is they are, or form part of, a globule.

The tissue-contacting members can be protuberances, nodules, raised dimples or globule such that the implant surface has a two dimensional array of protuberances, nodules or raised dimples. Thus, each of the protuberances, nodules, raised dimples or globule provides a convex curved tissue-contacting surface such that the cumulative effect of the array of such curved surfaces is to mimic the topography of the adipose tissue surface.

As noted above, the tissue-contacting members (protuberances, nodules or raised dimples) suitably have the shape of part of or all of a hemisphere. The inventors believe that the hemisphere is the shape that provides closest match to the native adipose tissue surface.

The height of the tissue-contacting members suitably corresponds to the height of a hemisphere having a radius of curvature corresponding to the radius of curvature of the convex curved tissue-contacting surface. Thus, the height suitably corresponds to the radius of the hemisphere.

Suitably the height of the tissue-contacting members varies. That is, the plurality of tissue-contacting members include tissue-contacting members of different heights such that there is height variation within the population of tissue-contacting members.

Suitable mean average height values are in the range 1 to 200 µm, suitably 1 to 150 µm, suitably 5 to 150 µm, suitably 10 to 150 µm, suitably 15 to 150 µm, suitably 15 to 130 µm, suitably 15 to 120 µm, suitably 15 to 110 µm, suitably 15 to 100 µm, suitably 15 to 90 µm, suitably 15 to 80 µm, suitably 15 to 70 µm, suitably 15 to 60 µm, suitably 15 to 50 µm, suitably 15 to 45 µm, suitably 15 to 45 µm, suitably 25 to 45 µm, suitably 30 to 45 µm, suitably 30 to 42 µm, suitably 32 to 42 µm, suitably 34 to 42 µm, suitably 34 to 40 µm, suitably 35 to 40 µm, suitably 36 to 40 µm, suitably about 38 µm. It will be clear from the preceding ranges that a suitable lower limit for mean average height is 1 µm, suitably 5 µm, suitably 10 µm. In the case of spaced-apart tissue-contacting members, the height is measured from the "base" surface located between the tissue-contacting members. In the case of hemispherical members, the height corresponds to the radius of the hemisphere.

Suitably at least 30% of the population of the tissue-contacting members fall within the height range of 1 to 200 µm, suitably 1 to 150 µm, suitably 5 to 150 µm, suitably 5 to 150 µm, suitably 5 to 150 µm, suitably 15 to 130 µm, suitably 15 to 120 µm, suitably 15 to 110 µm, suitably 15 to 100 µm, suitably 15 to 90 µm, suitably 15 to 80 µm, suitably 15 to 70 µm, suitably 15 to 60 µm, suitably 15 to 50 µm, suitably 15 to 45 µm, suitably 20 to 45 µm. It will be clear from the preceding ranges that a suitable lower limit for the height is 1 µm, suitably 5 µm, suitably 10 µm. Suitably at least 40% of the population of the tissue-contacting members fall within this height range, suitably at least 50% of the population, suitably at least 60%, suitably at least 70%, suitably at least 80%, suitably at least 90%.

In embodiments where the tissue-contacting members are not spaced apart and there is no space between the tissue-contacting members that can be regarded as a "base" surface, a notional base surface/plane can be obtained with reference to height profile information (of the sort shown in FIGS. 10-1B and 10-2B, obtained from laser confocal imaging data), with the notional base surface/plane being plotted to coincide with the troughs/valleys between the peaks. In such a case the mean average height values are suitably selected from the ranges as set out above and the following ranges: suitably 1 to 200 µm, suitably 1 to 150 µm, suitably 5 to 150 µm, suitably 5 to 130 µm, suitably 5 to 120 µm, suitably 5 to 110 µm, suitably 5 to 100 µm, suitably 5 to 90 µm, suitably 5 to 80 µm, suitably 5 to 70 µm, suitably 5 to 60 µm, suitably 5 to 50 µm, suitably 5 to 45 µm, suitably 5 to 45 µm, suitably 5 to 45 µm, suitably 5 to 45 µm, suitably 5 to 40 µm, suitably 5 to 35 µm, suitably 5 to 32 µm, suitably 5 to 30 µm, suitably 5 to 28 µm, suitably 5 to 25 µm, suitably 10 to 40 µm, suitably 10 to 35 µm, suitably 10 to 30 µm, suitably 15 to 40 µm, suitably 15 to 35 µm. It will be clear from the preceding ranges that a suitable lower limit for mean average height is 1 µm, suitably 5 µm, suitably 10 µm.

Suitably at least 30% of the population of the (non-spaced apart) tissue-contacting members fall within the height range of 1 to 200 µm, suitably 1 to 150 µm, suitably 5 to 150 µm, suitably 5 to 130 µm, suitably 5 to 120 µm, suitably 5 to 110 µm, suitably 5 to 100 µm, suitably 5 to 90 µm, suitably 5 to 80 µm, suitably 5 to 70 µm, suitably 5 to 60 µm, suitably 5 to 50 µm, suitably 5 to 45 µm, suitably 5 to 45 µm, suitably 5 to 45 µm, suitably 5 to 45 µm, suitably 5 to 40 µm, suitably 5 to 35 µm, suitably 5 to 32 µm, suitably 5 to 30 µm, suitably 5 to 28 µm, suitably 5 to 25 µm, suitably 10 to 40 µm, suitably 10 to 35 µm, suitably 10 to 30 µm, suitably 15 to 40 µm, suitably 15 to 35 µm. It will be clear from the preceding ranges that a suitable lower limit for the height is 1 µm, suitably 5 µm, suitably 10 µm. Suitably at least 40% of the population of the tissue-contacting members fall within this height range, suitably at least 50% of the population, suitably at least 60%, suitably at least 70%, suitably at least 80%, suitably at least 90%.

The underlying surface of the implant material, on which the implant surface is overlaid, may be flat or not flat. For example, as discussed above, the implant material may have a curved shape, e.g. to conform to the shape of the implant.

Suitably the surface coverage of the tissue-contacting members, being the extent to which the implant surface is covered by/provided by the tissue-contacting members, is at least 20% (')/0 of total implant surface area covered). The surface coverage can be ascertained by taking measurements from suitable images of the surface, for example an SEM image. Suitably the surface coverage of the tissue-contacting members is at least 30%, suitably at least 40%, suitably at least 50%, suitably at least 60%, suitably at least 70%, suitably at least 80%, suitably at least 90%, suitably at least 95%, suitably at least 98%, suitably at least 99%, suitably about 100%. Suitably the number of tissue-contacting members, their size and placement, is such that the majority, suitably at least 60%, suitably at least 70%, suitably at least 80%, suitably substantially all, suitably all of the implant surface is provided by the convex curved tissue-contacting surfaces of the tissue-contacting members.

This "high density" coverage is believed to be a particularly effective mimic of the adipose tissue surface.

Suitably the implant surface has 100 to 100000 tissue-contacting members per cm², suitably 100 to 50000, suitably 100 to 40000, suitably 200 to 40000, suitably 400 to 40000, suitably 500 to 40000, suitably 750 to 40000, suitably 900 to 35000, suitably 1000 to 35000, suitably 1200 to 35000, suitably 1500 to 35000, suitably 1750 to 32500, suitably 2000 to 30000, suitably 2250 to 30000, suitably 2250 to 27500, suitably 5000 to 40000, suitably 10000 to 40000, suitably 10000 to 30000, suitably about 25000 tissue-contacting members per cm². It will be clear from the preceding ranges that a suitable lower limit for the density (tissue-contacting members per cm²) of the tissue-contacting members is 100, suitably 500, suitably 5000, suitably 10000. It will be clear from the preceding ranges that a suitable upper limit for the density (tissue-contacting members per cm²) of the tissue-contacting members is 100000, suitably 50000, suitably 40000.

In embodiments the plurality of tissue-contacting members are discrete members, in the sense that they are spaced from each other. In embodiments the plurality of tissue-contacting members are not discrete members. Suitably they are adjacent each other, for example so as to appear to be merged or fused together.

Suitably the plurality of tissue-contacting members is a plurality of truncated hemispheres arranged to form a two-dimensional array of fused hemispheres.

Suitably the tissue-contacting members are close packed. Suitably the tissue-contacting members are arranged so as to have a packing structure corresponding to a layer in a close packed structure, especially selected from hexagonal close packed (hcp) and face centred cubic (fcc).

Suitably each tissue-contacting member has at least four, suitably at least five, suitably six neighbours (i.e. other tissue-contacting members).

Suitably each tissue-contacting member has at least four, suitably at least five, suitably six neighbours (i.e. other tissue-contacting members) within a distance corresponding to 2× the width (e.g. diameter) of the tissue-contacting member. A neighbour is deemed to be located within that distance if at least part of the neighbour is encompassed by an imaginary line defining a circle around the tissue-contacting member, which circle has a radius of, in the above case, 2× the width (e.g. diameter) of the tissue-contacting member. Suitably the distance corresponds to 1.5× the width (e.g. diameter) of the tissue-contacting member.

Suitably the tissue-contacting members are substantially symmetrical about an axis of rotation that is perpendicular to the implant surface (the Z direction extending vertically from the implant surface).

Suitably the tissue-contacting members are substantially free from edge features and/or corner features. Suitably the implant surface is substantially free from edge features and/or corner features.

Suitably the implant surface has valleys formed by two or more adjacent tissue-contacting members (E.g. adjacent (part) hemispherical members). Indeed, the truncation of adjacent tissue-contacting members can provide the valleys. Suitably the valleys are interconnected. That is, one valley is joined to one or more other valleys (suitably such other valleys themselves being formed by adjacent tissue-contacting members). Valleys may be joined end-to-end to form the interconnected network.

Two-dimensional array means that the tissue-contacting members are located in an array that extends in both linear directions parallel to the implant surface (X and Y directions). Thus, the provision of the convex curved tissue-contacting surfaces of the invention represents a fundamentally different approach to surface morphologies based on grooves.

Suitably the array is a substantially hexagonal array.

Suitably the two-dimensional array is a substantially regular two-dimensional array. This reflects the order in the adipose tissue surface, albeit that some deviation from true regularity exists. Nevertheless, even more regular/ordered arrays or irregular/disordered arrangements are possible.

Suitably the mean average centre-to-centre nearest neighbour spacing of the array of tissue-contacting members, $TCMcc_{AVE}$, is from 1 to 200 µm, suitably from 1 to 150 µm, suitably from 1 to 120 µm, suitably from 5 to 120 µm, suitably from 10 to 120 µm, suitably from 20 to 120 µm, suitably from 30 to 120 µm, suitably from 30 to 110 µm, suitably from 30 to 100 µm, suitably from 40 to 100 µm, suitably from 40 to 90 µm, suitably from 45 to 90 µm, suitably from 50 to 90 µm, suitably from 55 to 90 µm, suitably from 60 to 90 µm, suitably from 60 to 85 µm, suitably from 65 to 85 µm, suitably from 65 to 80 µm, suitably from 68 to 80 µm, suitably from 68 to 78 µm, suitably from 69 to 75 µm, suitably from 70 to 75 µm, suitably about 73 µm. It will be clear from the preceding ranges that a suitable upper limit for mean average centre-to-centre nearest neighbour spacing is 200 µm, suitably 150 µm, suitably 100 µm. The centre point of a tissue-contacting member is the centre point when the implant surface is viewed "top-down". In the case of (approximately) hemispherical tissue-contacting members the centre point is the centre of a circle whose circumference corresponds to the boundary of the tissue-contacting member in the X-Y plane (i.e. the relevant cross-section of the tissue-contacting member). In the case of other shapes, the centre point can be obtained by selecting a circle whose diameter is such that the circle encompasses the X-Y cross section of the tissue-contacting member (i.e. when viewed "top-down").

Suitably at least 30% of the population of the tissue-contacting members have a centre-to-centre nearest neighbour spacing in the range of from 1 to 200 µm, suitably from 1 to 150 µm, suitably from 1 to 120 µm, suitably from 5 to 120 µm, suitably from 10 to 120 µm, suitably from 20 to 120 µm, suitably from 30 to 120 µm, suitably from 30 to 110 µm, suitably from 30 to 100 µm, suitably from 40 to 100 µm, suitably from 40 to 90 µm, suitably from 45 to 90 µm, suitably from 50 to 90 µm, suitably from 55 to 90 µm, suitably from 60 to 90 µm, suitably from 60 to 85 µm, suitably from 65 to 85 µm, suitably from 65 to 80 µm. It will be clear from the preceding ranges that a suitable upper limit for mean average centre-to-centre nearest neighbour spacing is 200 µm, suitably 150 µm, suitably 100 suitably from 1 to 120 µm. Suitably at least 40% of the population of the tissue-contacting members fall within this range, suitably at least 50% of the population, suitably at least 60%, suitably at least 70%, suitably at least 80%, suitably at least 90%.

Suitably the mean average diameter of the plurality of tissue-contacting members, $TCMd_{AVE}$, is from 1 to 200 µm, suitably from 1 to 150 µm, suitably from 1 to 120 µm, suitably from 5 to 120 µm, suitably from 10 to 120 µm, suitably from 20 to 120 µm, suitably from 30 to 120 µm, suitably from 30 to 110 µm, suitably from 30 to 100 µm, suitably from 40 to 100 µm, suitably from 40 to 90 µm, suitably from 45 to 90 µm, suitably from 50 to 90 µm, suitably from 55 to 90 µm, suitably from 60 to 90 µm, suitably from 60 to 85 µm, suitably from 65 to 85 µm, suitably from 65 to 80 µm, suitably from 68 to 80 µm, suitably from 68 to 78 µm, suitably from 69 to 75 µm, suitably from 70 to 75 µm, suitably about 73 µm. It will be clear from the preceding ranges that a suitable upper limit for mean average diameter is 200 µm, suitably 150 µm, suitably 100 µm. The diameter of a tissue-contacting member can be obtained by following the methodology outlined above to obtain the centre point of the tissue-contacting member, whereby the circle selected in that method provides the diameter value for the tissue-contacting member.

Suitably at least 30% of the population of the tissue-contacting members have a diameter in the range of from 1 to 200 µm, suitably from 1 to 150 µm, suitably from 1 to 120 µm, suitably from 5 to 120 µm, suitably from 10 to 120 µm, suitably from 20 to 120 µm, suitably from 30 to 120 µm, suitably from 30 to 110 µm, suitably from 30 to 100 µm, suitably from 40 to 100 µm, suitably from 40 to 90 µm, suitably from 45 to 90 µm, suitably from 50 to 90 µm, suitably from 55 to 90 µm, suitably from 60 to 90 µm, suitably from 60 to 85 µm, suitably from 65 to 85 µm, suitably from 65 to 80 µm. It will be clear from the preceding ranges that a suitable upper limit for mean average centre-to-centre nearest neighbour spacing is 200 µm, suitably 150 µm, suitably 100 µm. Suitably at least 40% of the population of the tissue-contacting members fall within this range, suitably at least 50% of the population, suitably at least 60%, suitably at least 70%, suitably at least 80%, suitably at least 90%.

Suitably the implant surface is a closed surface. That is, it is substantially free, suitably completely free, of pores or other open structures. Thus, suitably the implant material is not an open cell or porous material. This does not preclude the bulk (i.e. underneath the surface) material having a porous or open structure.

The implant surface may also comprise a nano-scale texture. For example this can be achieved by the use of oxygen plasma etching as discussed herein. The inventors have found that the provision of such nano-texture mimics the corresponding texture on the hemispherical surfaces of adipose cells. Suitably the tissue-contacting surfaces of the tissue-contacting members comprise nano-scale features (e.g. ridges or peaks) having a height (as measured e.g. by AFM) in the range from 200 to 800 nm, suitably 300 to 700 nm. Suitably the mean height of these features is in the range from 200 to 800 nm, suitably 300 to 700 nm, suitably 400 to 600 nm.

Surgical Use

The inventors envisage non-cosmetic use of the implant material. For example, in reconstructive surgery or breast augmentation, for example following oncologic surgery or injury.

The implant material disclosed herein, suitably as part of an implant, may be placed subcutaneously, subfascially or submuscularly. In the case of a breast implant, the implant may be located in the tissue plane between the adipose tissue of the breast (anteriorly) and the pectoralis muscle fascia (posteriorly).

Cosmetic Use

The implant material of the invention can be used in cosmetic methods, for example a cosmetic breast enlargement method.

Such methods may comprise the step of implanting into the human body an implant comprising the implant material as disclosed herein.

Implant Material

In embodiments of any of the aspects herein the implant material comprises, suitably comprises as a major component (e.g. at least 50 wt % of the total weight of the implant material, preferably at least 60 wt %, more preferably at least 70 wt %, more preferably at least 80 wt %, more preferably at least 90 wt %) in embodiments consist substantially of, in typical embodiments consist of, a suitable biocompatible material.

Suitably the material is capable of being shaped, e.g. by casting etching and/or moulding into a textured surface. Suitably, the material may comprise suitably comprises as a major component (e.g. at least 50 wt % of the total weight of the implant material, preferably at least 60 wt %, more preferably at least 70 wt %, more preferably at least 80 wt %, more preferably at least 90 wt %, more preferably at least 95 wt %, more preferably at least 99 wt %) in embodiments consist substantially of, typically consist of, a biocompatible synthetic polymer, suitably an organo-silicon polymer, preferably a silicone, and more preferably polydimethylsiloxane (PDMS).

It is particularly preferred that the surface of the implant material for which surface roughness parameters are specified herein (i.e. the surface intended to contact the patient's tissue, i.e. the tissue-engaging surface) comprises the above-mentioned biocompatible synthetic polymer. Indeed, as noted above, suitably the surface consists substantially of an organo-silicon polymer, preferably PDMA. Thus, in embodiments, the surface (tissue-engaging surface) is a textured organo-silicon surface, the texture being as described herein.

Suitably the composition of the implant material is substantially homogeneous, especially in a depth direction from the surface (tissue-engaging surface) into the bulk material.

The implant material suitably forms at least part of the surface layer of the relevant implant. Thus, surfaces of implants of the invention may partly comprise conventional implant surfaces as well as the novel and advantageous surfaces described herein. In embodiments, the implant material surfaces of the invention described herein forms at least half, in suitable embodiments more than half, preferably substantially all (e.g. at least 90%, 95%, 98% or 99% by area of the implant surface) of the tissue contacting surface of the implant, such as wherein the tissue contacting surface of the implant consists of said implant material. The material comprising the surfaces of the invention may be different to other materials in the implant or may be the same. Thus the implant may comprise an underlayer layer of the same of different material to the implant surface layer of the invention.

The implant may be any suitable implant capable of insertion into a patient, preferably a prosthetic implant, optionally an implant for internal insertion beneath the skin surface of a patient, more preferably a breast implant.

As noted above, the implant materials of the present invention are preferably configured so as to be inserted subcutaneously within a patient or may be administered externally. Preferably the implant is administered (is intended to be located) internally, e.g. subcutaneously, subfascially or submuscularly.

Templates

In a further aspect of the invention is provided a template for use in preparing an implant material according to any aspect or embodiment herein. Suitably, said template comprises a textured surface as described according to any aspect or embodiment herein, or a negative (e.g. an inverse cast) of a textured surface as described herein. The template may typically comprise the 3-dimensional information, i.e. X,Y,Z information, corresponding to the implant material surface of the invention as defined according to any aspect and embodiment herein. In embodiments, the template is a stamp or mould, e.g. a stamp for imprinting a surface texture of the invention onto an implant surface or moulding the implant surface, optionally wherein the stamp or mould is a silicone stamp or mould. Thus, a surface may be stamped or moulded a number of times to provide an implant material having a surface as defined above. In embodiments, the template itself is a mould. The use of moulds is beneficial as they can be used to manufacture a large number of implants quickly.

Methods

In an aspect of the invention is provided a method of preparing an implant material having a textured surface comprising the steps of acquiring spatial data in the X, Y and Z dimensions (i.e. three-dimensional spatial data) from an adipose tissue surface and using said spatial data to create the textured surface of the implant.

Suitably, the use of the spatial data further comprises the step of processing the spatial data and using the processed data to create the textured surface of the implant.

The inventors thus propose the acquisition of 3D image/topography data corresponding to an adipose tissue surface for reproduction on (formation of) an implant surface. This approach represents a considerable departure from conventional approaches to texturising implant surfaces, which are largely based on trial and error application of crude and often irreproducible methods which do not provide suitable control of the implant surfaces produced (e.g. by making open cell foam or by texturising using salt methods).

In embodiments, the step of acquiring the spatial X,Y,Z data is performed by any suitable contact or non-contact profilometer, suitably by atomic force microscopy, 3D laser scanner or optical profiler.

In embodiments, the step of creating the textured surface using the spatial X,Y,Z data includes three dimensional printing or photolithography or E-beam lithography, particularly optical photolithography, e.g. UV lithography, e.g. using a laser writer. In an embodiment, the method includes the step of processing the 3D data (spatial X,Y,Z) by converting, suitably digitally converting the respective data to a form of data that can be read by a maskless lithography system. In an embodiment, the processing step includes formation of a two or more 8 bit (or optionally 16 bit) grayscale image wherein the 256 (e.g. or optionally 65536) different grayscale intensities corresponds to changes in vertical height of a measured surface. Alternatively or additionally, the processing step includes joining two or more grayscale images (maps) to form a mosaic montage of surface images prior to applying the image to a surface, for example prior to assigning a number of radiation doses on every pixel and thus controlling the exposure of the photoresist.

Use of such methods thus allows the production of controlled surface features in an implant surface, which are, based on the reproduction of surface features taken from an adipose tissue environment and not from surfaces manufactured by the crude and uncontrolled ways reported in prior art. The method is more versatile than prior art methods and adaptation of the digital X,Y,Z information can provide not only the cell topography itself, but a variety of surface topographies using the adipose tissue surface features as the original inspiration. Processing and manipulation of the surface data during the lithography or printing allows for reproduction of an endless range of surface designs.

Use of Electron Beam (E-beam) Lithography may allow the reproduction of features that are <50 nm in lateral resolution. Thus, in an embodiment, the process of forming the surface of the invention from using the spatial X,Y,Z data includes using Electron Beam (E-beam) Lithography.

In embodiments, the method further comprises using the spatial X,Y,Z data to expose a photoresist (for example an E-beam photoresist) comprising the respective X,Y,Z information.

The method suitably includes use of the exposed and developed photoresist (for example an E-beam resist) to form the textured surface. The step of using the exposed and developed photoresist to transfer the textured surface onto a template may optionally comprise using an etching method, optionally oxygen etching and/or deep reactive ion etching.

Embodiments of the method include use of the spatial X,Y,Z data to expose the photoresist and/or an e-beam resist comprising using the spatial X,Y,Z data to instruct the delivery of varying doses of radiation to a photoresist and/or E-beam resist surface so as to expose a photoresist and/or E-beam resist comprising the respective X,Y,Z information. Usually photolithography methods for preparing 3D features in objects (such as commonly used in the semiconductor industry) use a graded photomask to control the relative intensity of radiation received by various parts of the photoresist during the photolithography step. However, it is expensive and time-consuming to prepare such photomasks and once made, they cannot be varied and must be used to make a range of identical patterns. To the contrary, the use of the X,Y,Z data (e.g. the colour or grayscale depiction of peak-trough height) to control the relative intensity of radiation received at a given point of the photoresist (such as by using laserwriter configured to read such grayscale data) can advantageously allow for the exposure of a photoresist having, after development, the surface features directly rather than using a photomask. In other words, in embodiments, the lithography method is a maskless lithography method.

In embodiments, the step of preparing the photoresist includes increasing or decreasing the scale of the original X, Y and/or Z parameters for reproduction in the photoresist. This may be used advantageously if the photoresist needs to be thinner in the vertical direction that the vertical features of the surface being reproduced. The features may this be scaled up again during another step, such as using etching, e.g. deep reactive ion etching.

In another aspect is a method of preparing an implant material having a textured surface comprising the step of making a cast of an adipose tissue surface, the cast containing spatial data representing the X, Y and Z dimensions and using said cast to make the textured implant material.

Method of Applying Texture to the Surfaces of the Invention

In embodiments, the method comprises the step of preparing said textured implant material surface by etching, stamping or moulding. In embodiments, the method comprises the step of preparing said textured implant material surface by etching. In embodiments the method comprises the step of preparing said textured implant material surface by stamping, optionally multiple stamping of a single surface to produce a textured surface having a number of stamped irregular textured regions, e.g. wherein the stamped images cover at least half, suitably more than half, and in embodiments substantially all of the implant surface configured to contact a patient's tissue when inserted. In embodiments the method comprises the step of preparing said textured implant material surface by moulding.

In embodiments the implant material prepared by said method is an implant material as described in any one of the aspects and embodiments of the invention described herein.

Data Set

In an aspect of the invention is the use of spatial data representing the X, Y and Z dimensions acquired from an dispose tissue surface in a method of preparing a textured material or a photoresist for use in preparing a textured material. In embodiments, the textured material is a textured implant material as described herein or a template as described herein.

In an aspect of the invention is a method of processing and/or modifying spatial data in the X, Y and Z dimensions, suitably so as to provide a data set capable of being used by a printer, for example a laser writer or 3D printer.

In embodiments, the use includes wherein the spatial data acquired from the adipose tissue surface is processed before use in said method of preparation.

In an aspect of the invention is spatial data in the X, Y and Z dimensions acquired from an adipose tissue surface.

In an aspect of the invention is a data carrier, suitably a computer readable data carrier, comprising spatial data as defined herein.

Tissue

In the above methods and uses, the tissue (i.e. the tissue from which spatial data is the X, Y and Z dimensions has been obtained or is representative of) is adipose tissue, preferably adipose tissue of the breast.

Through mimicking the topographical cues of adipose tissue onto the surface of a silicone implant, cells that encounter it attach and stabilize without becoming stressed and transforming into a pro-inflammatory/fibrotic phenotype resulting in the initiation of chronic inflammation and fibrosis around the implant through attraction and activation of neutrophils and macrophages.

Consequently, it is thought that the extent of the foreign body reaction and subsequent capsular contracture formation would be potentially averted.

Whilst it is understood that adipose tissue may be able to effect such functions in the body, it is entirely surprising that the excellent results achieved using the fabricated materials prepared would show the excellent results observed when the 3D topographic features were reproduced in silicone implant surfaces as discussed in the examples section.

Further Aspects

In a further aspect is provided an implant material comprising a textured surface as prepared by a method as defined according to any aspect or embodiment herein.

Also provided is a template for use in preparing an implant material of the invention as described herein, said template having textured surface parameters as defined herein, or a negative of said textured surface parameters, optionally wherein the template is a mould or stamp, such as defined above.

The invention also provides the use of a template as described herein in a method of making a textured implant material. Typically the template is a silicone template, most preferably PDMS.

Also provided is a cosmetic method comprising the step of inserting an implant material as described in any of the aspects and embodiments of the invention disclosed herein subcutaneously in a patient. Suitably said method is so as to provide minimal or no capsular contraction and/or cellular immunogenic response. Furthermore, in embodiments the method is for reconstructions of the breast.

General

The term "comprising" encompasses "including" as well as "consisting" e.g. an implant "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

The use of the term "irregular" in the context of the surfaces of the present invention will be well understood by the skilled person. Suitably, the term "irregular" in the context of the surfaces of the present invention refers to surface areas which are devoid of regular geometric patterns (such as repeating patterns), such as at the relevant macro, micro and/or nano scales (such as at the 1 cm×1 cm, 1 mm×1 mm, 100 micron×100 micron and/or at sub-micron level). The term "irregular" in the context of the surfaces of the present invention thus includes surfaces which appear to be disordered.

It will be appreciated on reading the present application that the surface of implants prepared according to the present invention may be formed by use of a stamp having an irregular textured surface which imparts its irregular surface topography to the implant on stamping. The stamp may thus be used repeatedly over the surface of the implant to ultimately provide up to complete surface coverage consisting of the substantially repeated irregular surface imprinted by the stamp. It is thus intended that the term "irregular" within the meaning of the present invention includes surfaces which have more than one, such as a plurality of repeating areas of such irregular surface topography.

The invention is described in more detail by way of example only with reference to the following Examples and experimental procedures.

Materials and Methods 2 biomimetic surfaces have been created, the "original adipose" and the "modelled adipose" surface. Tissue samples used in this study were obtained through the Plastics and Reconstructive Surgery Research (PRSR) Skin and Tissue Bank ethics (North West Research Ethics Committee Ethics Code—11/NW/0683). Informed consent was obtained from patients for the use of their tissue in this study. All breast tissue processing was done at our Human Tissue Authority licensed laboratory. The following describes the characterisation and fabrication of two novel polydimethysiloxane (PDMS) implant surfaces derived from native breast tissue topography.

Collection of Breast Tissue and Sample Fixation

Breast tissue from three patients was collected from elective cosmetic breast reduction operations and transported to our lab in Dulbecco's Modified Eagle Medium (Sigma-Aldrich, UK) supplemented with 1% penicillin and streptomycin (PAA laboratories, Pasching, Austria), 1% L-glutamine (PAA) and 10% Fetal Bovine Serum (PAA). Patients had no past medical history of any malignancy or fibrotic conditions, none were obese and none smoked.

Breast tissue was washed thoroughly in warmed phosphate buffered saline (PAA) supplemented with 1% Penicillin and Streptomycin (PAA) before the lobules of breast adipose tissue were dissected from the breast tissue samples. Lobules of the breast tissue were dissected and fixed in paraformaldehyde 2% (Sigma-Aldrich), glutaraldehyde 2.5% (Sigma-Aldrich) and 0.1M hepes buffer (Formedium, UK) for 7 days at 4° C.

Adipose tissue was washed four times in distilled water for 15 minutes each and then post fixed in osmium tetroxide 1% (Agar Scientific, UK) in 0.1M hepes (Formedium) for 1 hour. Following two further wash steps in distilled water of 15 minutes each, the tissue was dehydrated using graded acetone steps of 25%, 50%, 75%, 90%, and 100%, for 15 minutes at each step. Three further washes in 100% acetone were then performed before the tissue was critical point dried (Quorum Technologies Ltd. East Sussex, England).

Imaging, Sample Measurement and Generation of "Original Adipose Surface"

For laser confocal imaging, fixed adipose tissue was mounted on a scanning electron microscopy (SEM) stub and measured using an X-100/X-200 series 3D laser confocal microscope with a 50× objective (Keyence, Japan). The surface of the adipocytes was measured using a Dimension Icon microscope (Bruker, USA), Quantitative Force mapping using a SCANASYST-FLUID+ tip (silicon nitride, nominal k=0.7) (Bruker). For Scanning Electron Microscopy (SEM), mounted samples were sputter coated with gold and palladium for 120 seconds using a SC7620 sputter coater (Quorum Technologies Ltd, UK) and imaged using an FEI (Oregon, USA) Quanta 250 FEG SEM.

Figure 3:
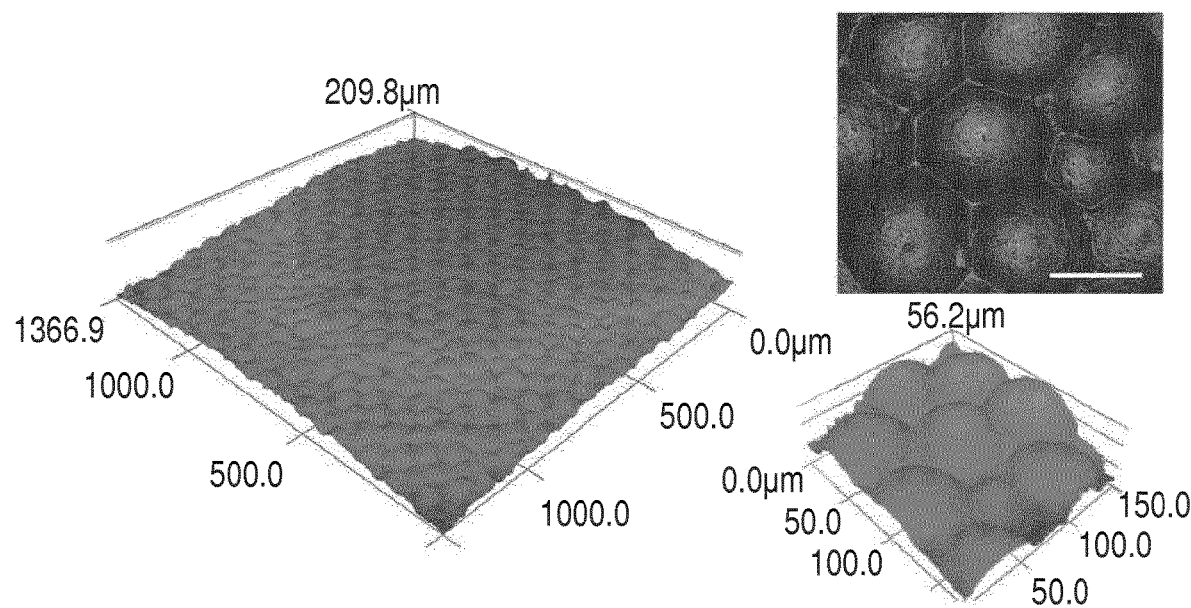
FIG. 3 is a laser confocal Height Map of Native breast tissue.

Images from the laser confocal microscope was then exported as an .asc point group data file. This .asc file was opened in Gwyddion. Image background subtraction using a polynomial fit function was used before the data was converted into an 8 bit grayscale bitmap, containing the height data in this file as 256 grayscales. This created the "Original Adipose" surface. (FIG. 3).

Measurement of the Adipose Surface

Figure 5:
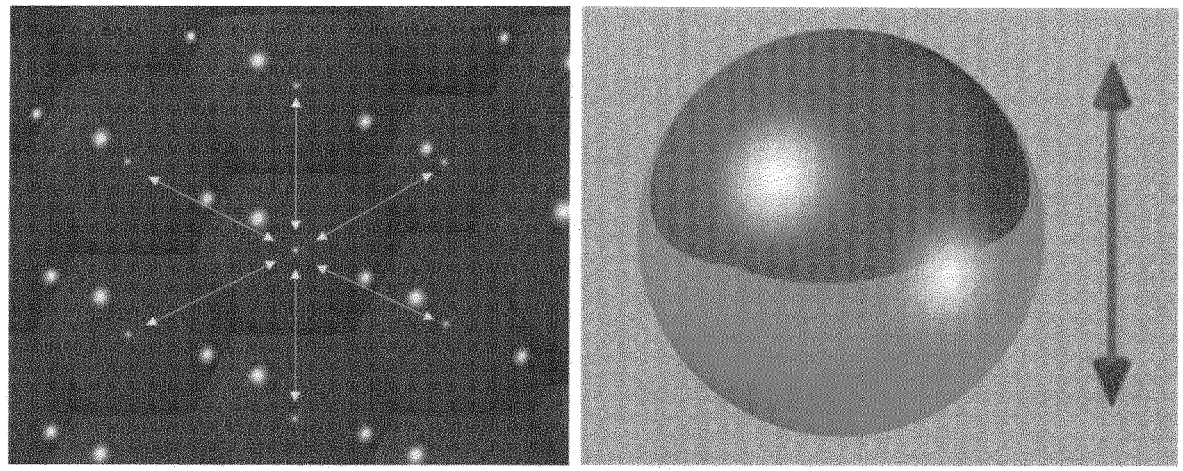
FIG. 5 is a schematic of "Nearest neighbour" distance and "Diameter".

The "Original Adipose" surface was further analysed to define its statistical characteristics. Matlab code was engineered to recognise boundaries between each hemisphere within these images. This was achieved through watershed segmentation (see FIG. 6C). The maximal height of each of these segments was then established by the code to recognise the centroid position of each hemisphere within these segments, before a 3D sphere fit function established the closest fit of a sphere to each segment. Code also generated data for the nearest neighbour distance (the distance between one centroid and the next) and hemisphere diameter. (FIG. 5)

Matlab Code Defines an "Modelled Adipose" Surface

Figure 6A:
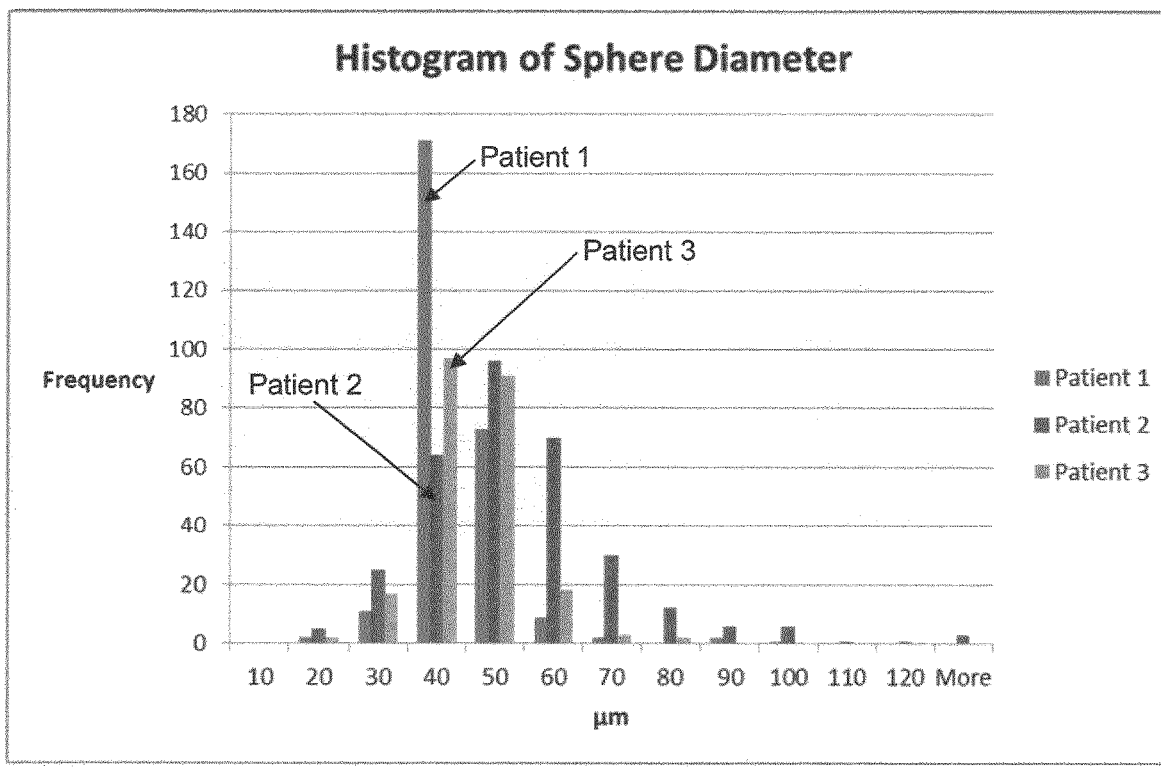
FIG. 6A is a histogram of Sphere diameter.
Figure 6C:
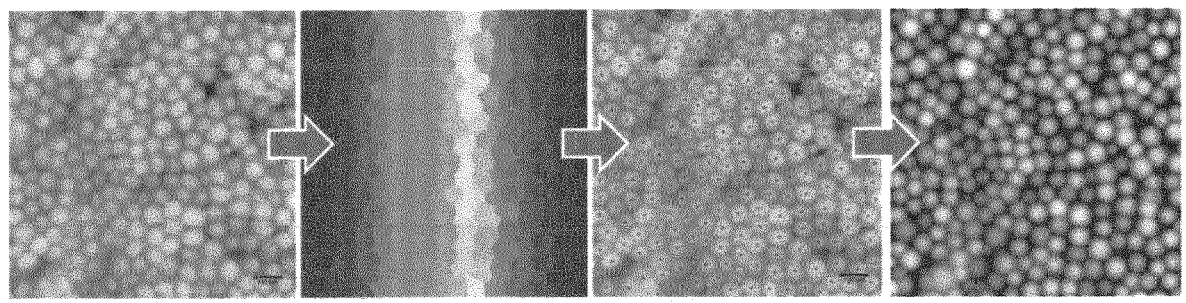
FIG. 6C is a demonstration of Matlab analysis process flow (left to right): (A) Original bitmap of breast tissue; (B) Division of A using thresholding of surface; (C) Centre point of thresholded areas from B; and (D) Generated bitmap of spheres with the same statistical properties as A (scale bars=100 µm).
Figure 7:
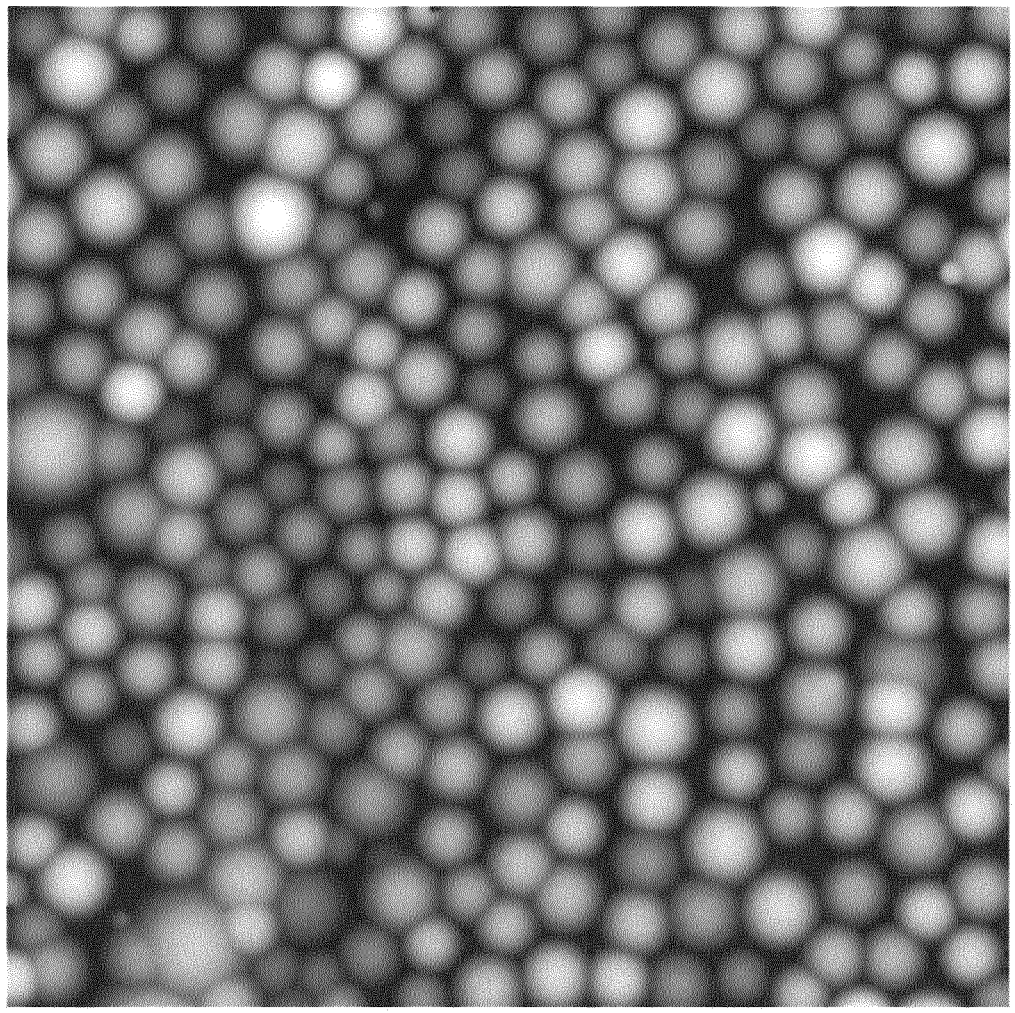
FIG. 7 shows Matlab defined image.
Figure 8A:
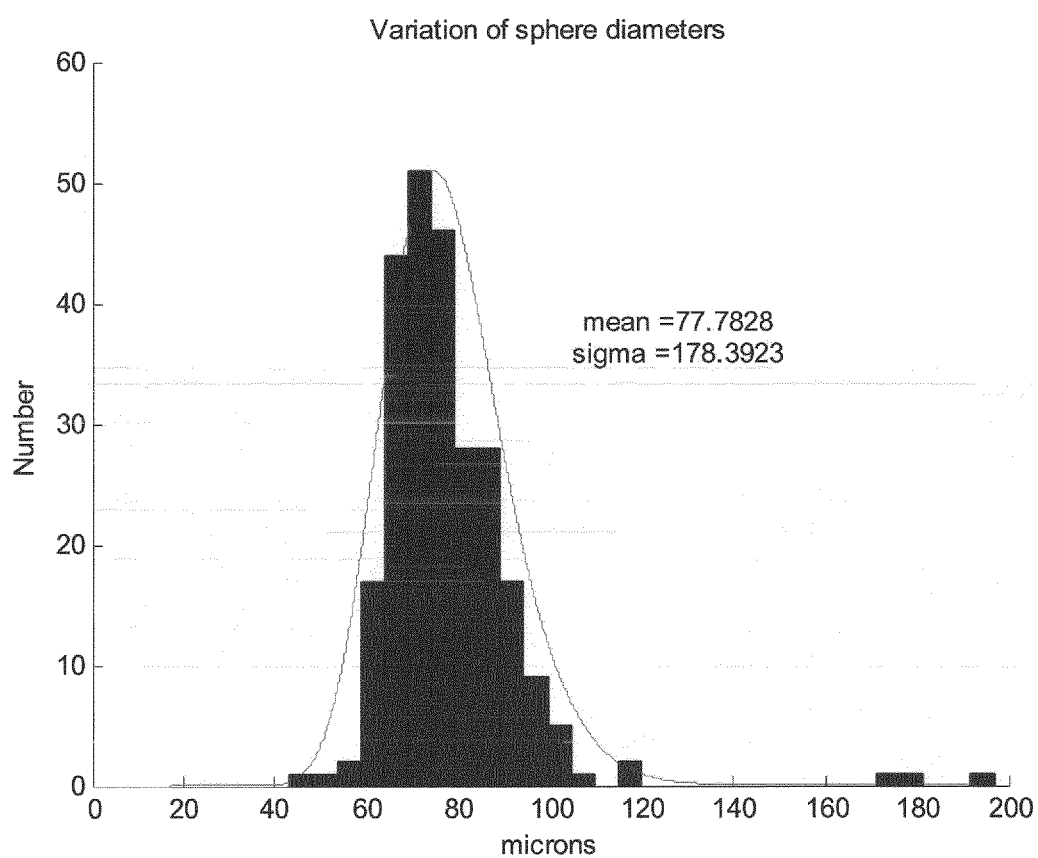
FIGS. 8A, 8B and 8C show statistical information obtained from the model surface.
Figure 8B:
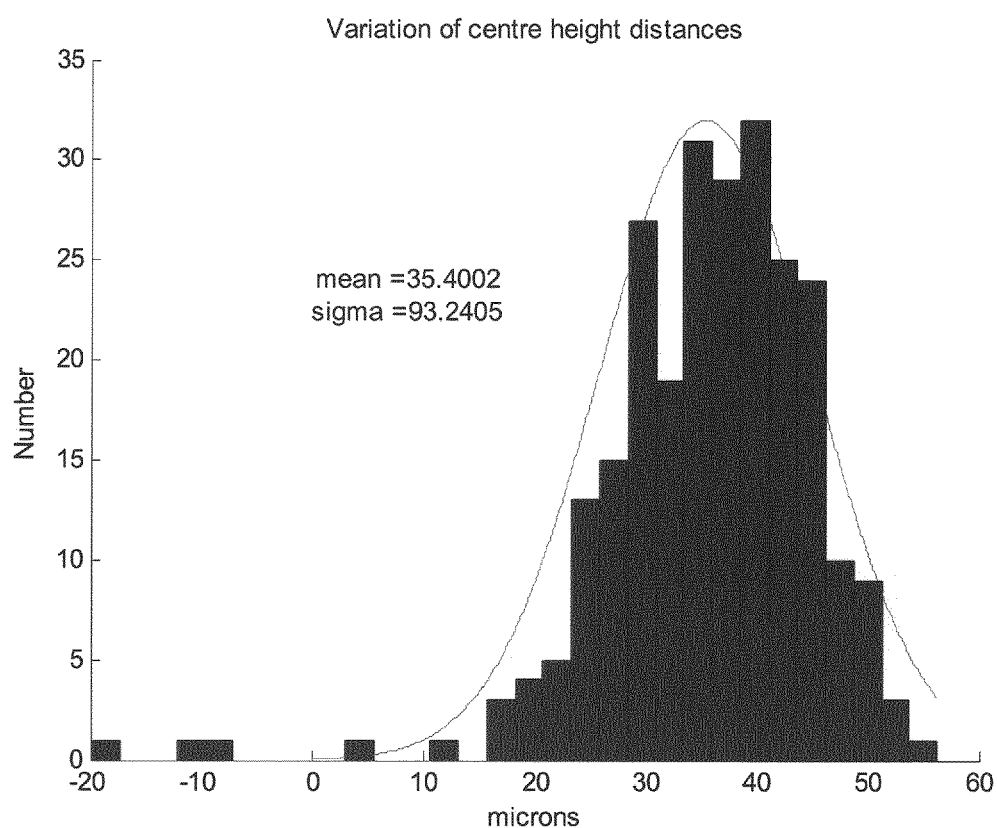
Figure 8C:
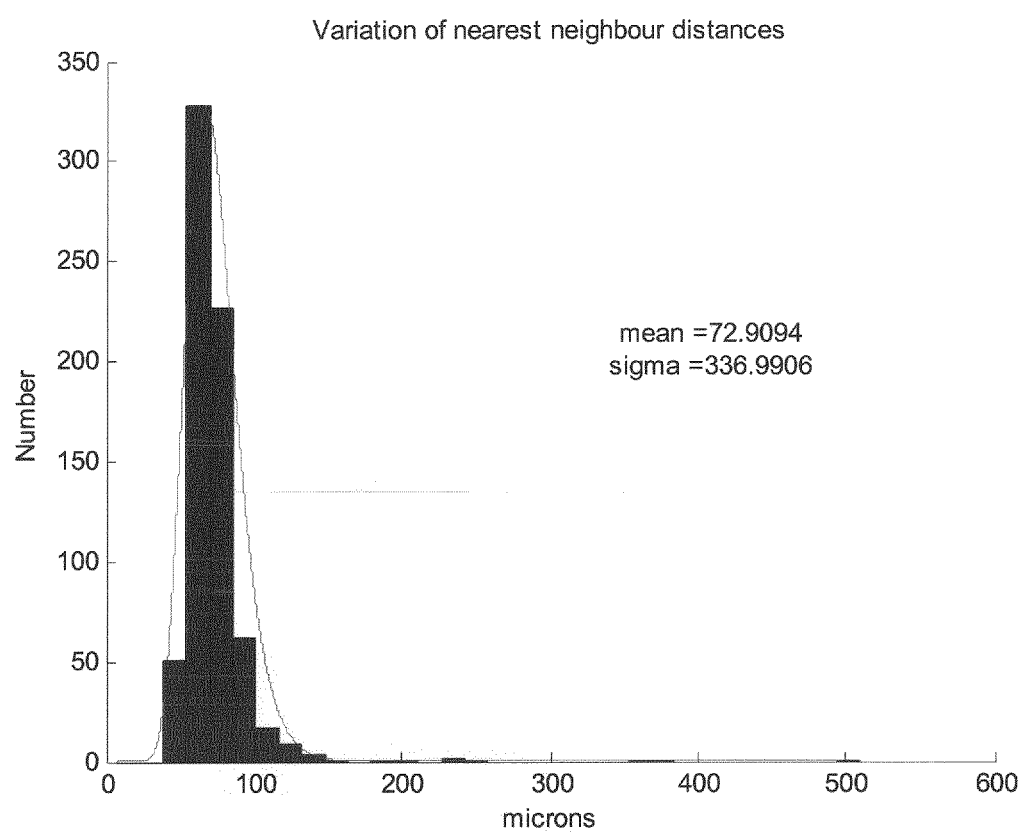
Figure 9A:
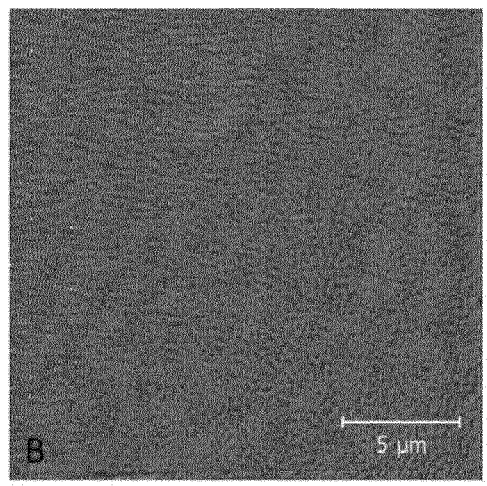
FIG. 9 shows the etched Modelled Surface.
FIG. 9B shows graph indicating nano-texture height correlation with etch recipe.
Figure 9B:
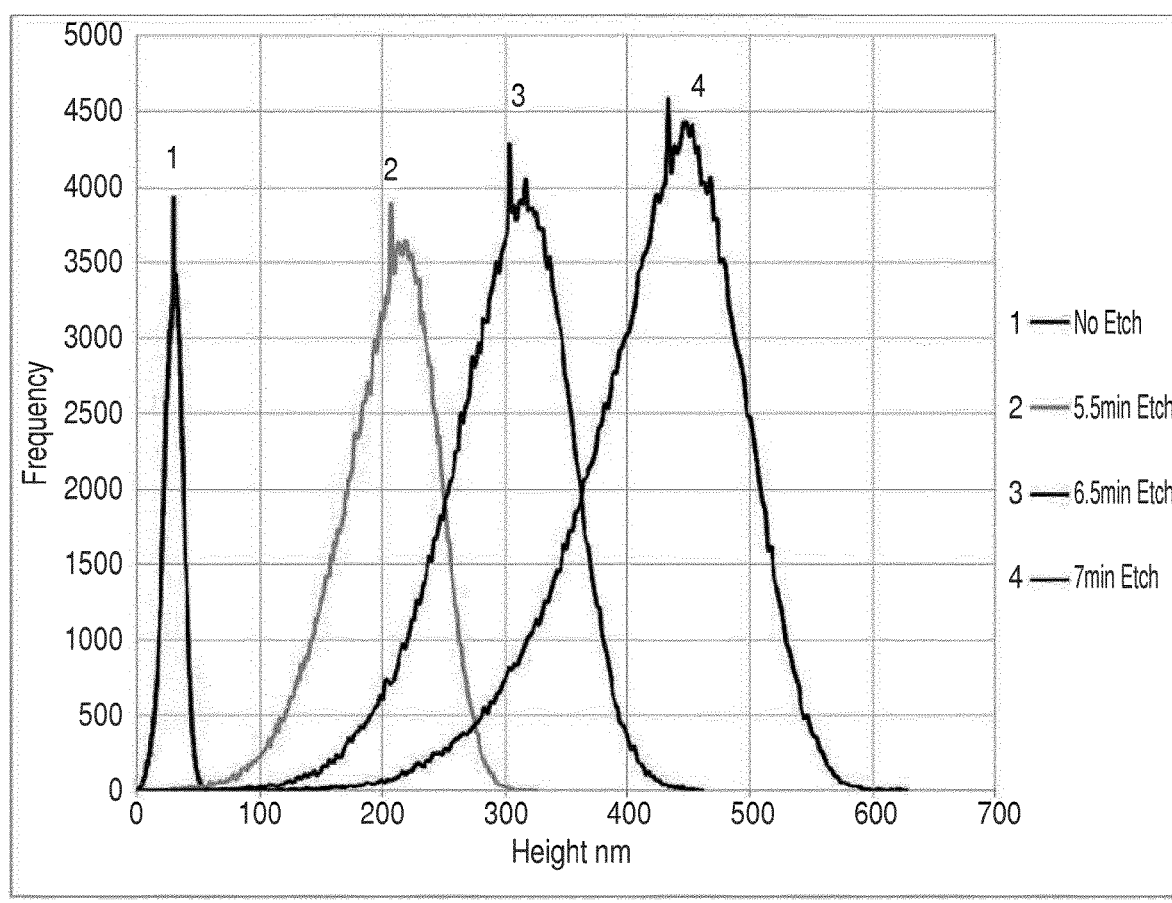

The Matlab code produced a surface, generated from the measurements taken from the "original adipose" surface. By combining the hemisphere diameter and relation of each hemisphere to its nearest neighbour a new "Modelled Adipose" surface was generated with the same statistical attributes as the native tissue. (FIG. 6C). This allowed the generation of a new "modelled adipose" bitmap image (FIG. 7). The "modelled adipose" surface had the same statistical attributes as that of the original adipose surface. The statistical data is shown with the log normal distribution fits in FIGS. 8A, 8B and 8C.

3D Photolithography

Figure 1:
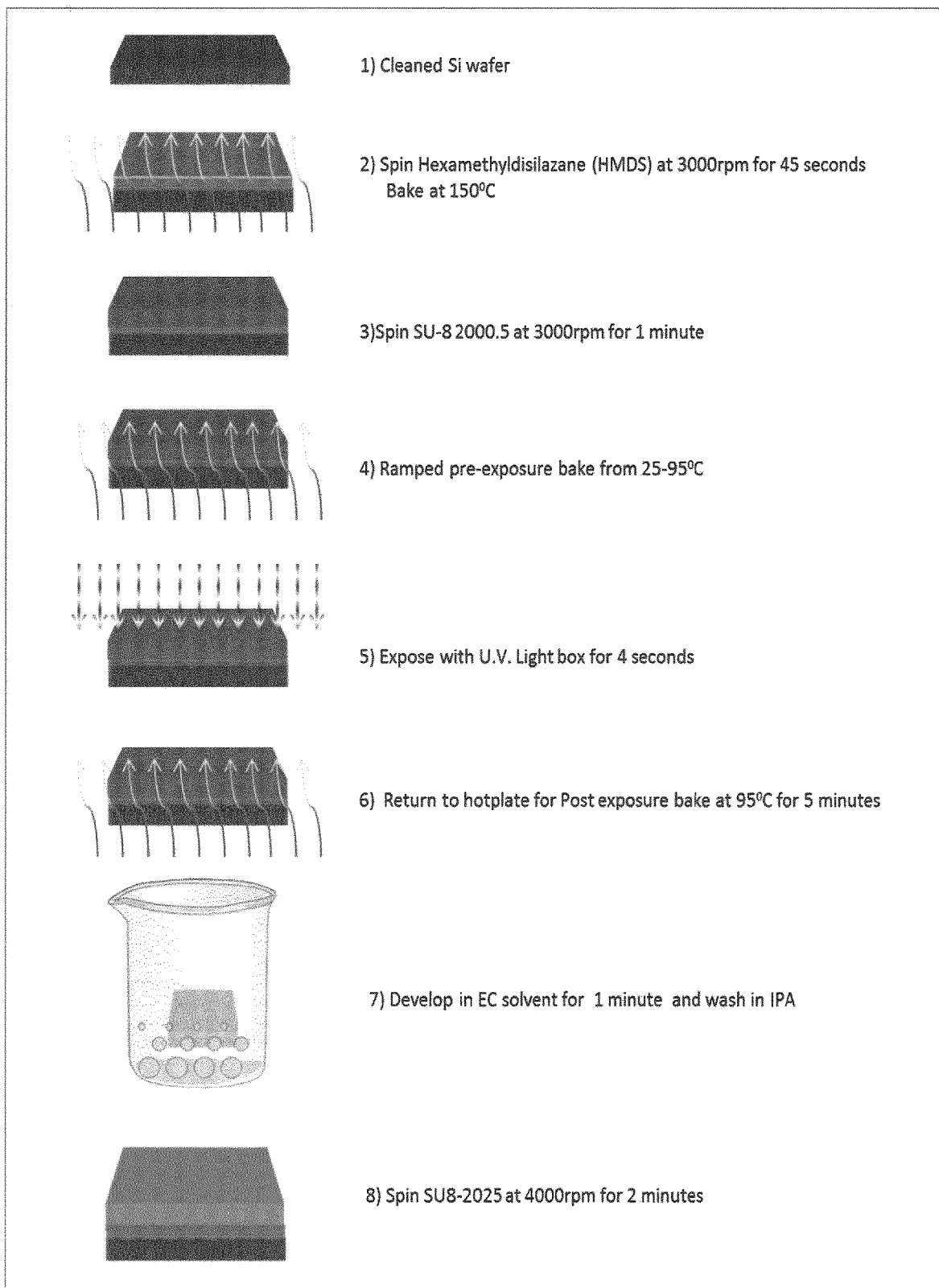
FIG. 1 shows a flow diagram of the manufacture process of the implant surfaces.
Figure 1:
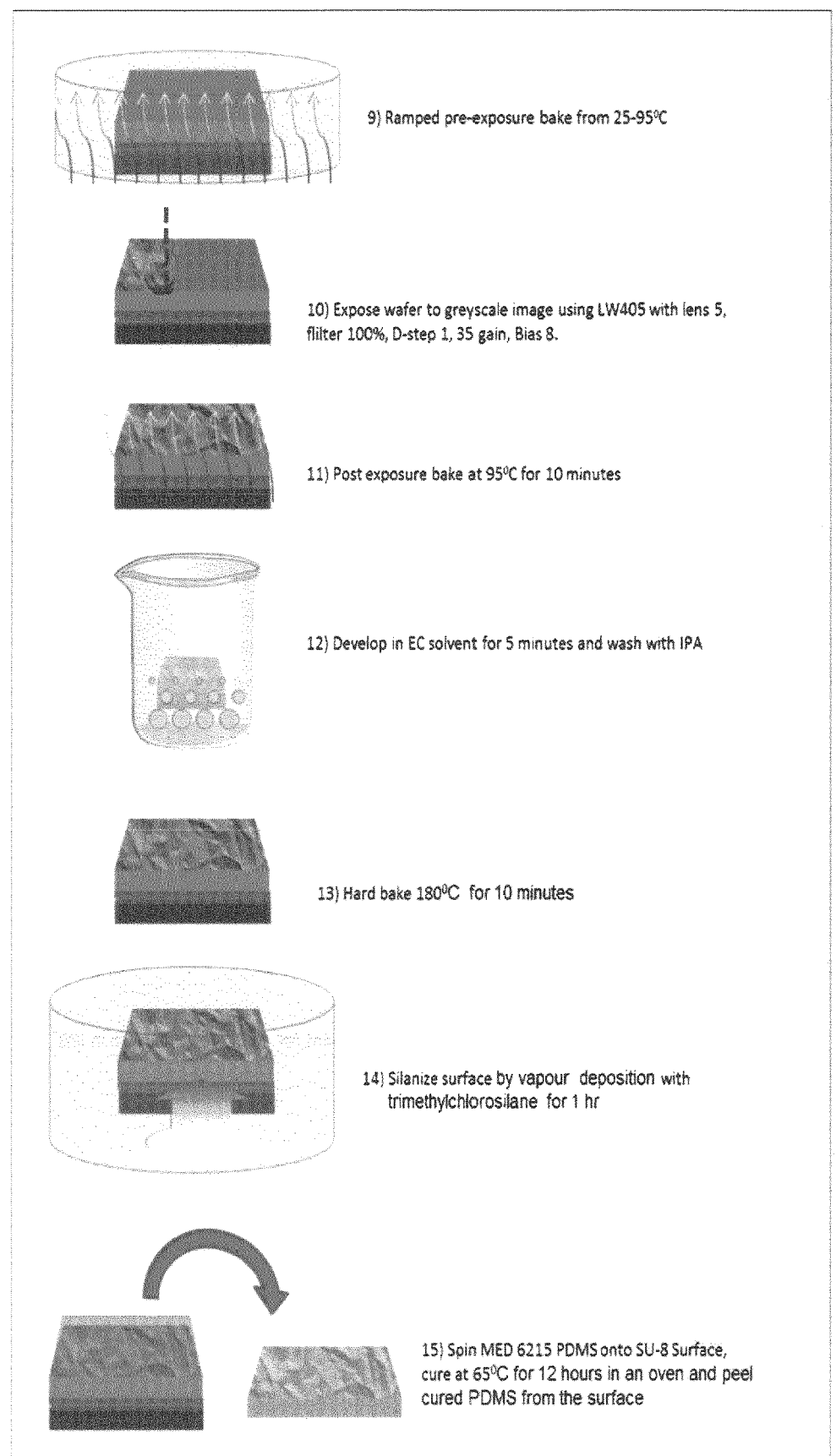

Following the generation of a bitmap of both the "original adipose" and Modelled adipose" surfaces these were transferred into PDMS using maskless grayscale lithography of a SU-8 photoresist mould illustrated in FIG. 1.

The Base Layer

In a class 100 clean room a 4×4 cm plain silicon wafer was sonicated for 10 minutes in acetone, isopropyl alcohol (IPA) and distilled water, dried with nitrogen gas and baked on a hot plate for 10 minutes at 150° C. Hexamethyldisilazane (Microchem, USA) was then spun onto the wafer at 3000 rpm for 45 seconds before it was returned to the hotplate for a further 10 minutes. As an adhesion layer, SU8-2000.5 (Microchem, USA) was spun onto the wafer at 3000 rpm and ramp baked from 25° C. to 95° C. before being held at 95° C. for 5 minutes. The SU-8 coated wafer was flood exposed to 454 nm wavelength light for 20 seconds before being returned to the hotplate for a further 5 minutes. The SU-8 coated wafer was developed in EC solvent for 1 minute before being rinsed in IPA and baked at 150° C. for 10 minutes.

The Surface Texture

A secondary, thicker layer, of SU-8 2025 (Microchem, USA) was then spun onto the surface of the base layer coated wafer at 4000 rpm, corresponding to a thickness of 30 µm. This was followed by a ramped pre-exposure bake from 25° C. to 95° C. before being held at 95° C. for 10 minutes.

Exposure

The wafer was exposed to either the "original adipose" or "modelled adipose" pattern using a laser writer (LW405 Microchem, Italy). Bitmap images were inverted prior to use using imageJ(19). Inverted bitmap images were loaded into the laserwriter software and pixel size was registered to 0.5 µm in X and Y. A 40× objective was used to expose the photoresist and laser power dose was dictated by the corresponding grayscale level (0 being no dose and 256 being maximum dose). Optimisation was performed on a grayscale wedge design and bitmap images were re-formatted using a code in Matlab to improve the linearity of the photoresist.

Development

Once the pattern had been transferred, the wafer was subject to a post exposure bake for 10 minutes at 95° C. before development of the pattern in MIcroposit EC solvent (Chestech Ltd, UK) for 10 minutes with gentle agitation. Substrates were then rinsed in IPA.

Secondary Texture

In the case of the Modelled Adipose surface, to impart a roughness onto the surface which had statistically similar properties to that of native adipose tissue, an oxygen etch recipe was used to texture the surface of the SU-8 master. An Oxford Plasmlab System 100 (Oxford, England) was used to etch the SU-8 surface for 6.5 minutes at 5 mTorr of pressure, with an RF power of 5, ICP pressure of 300 and an O2 flow rate of 45 Sccm.

Trimethylchlorosilane Vapour Acts as a Release Layer Between Silicone and Master Mold To passivize the surface of the SU-8 mould, to reduce silicone bonding to this master template, trimethylchlorosilane (TMCS, Sigma, UK) was used. The SU-8 master and 0.5 mls of TMCS were placed under vacuum to vaporise the TMCS. The vacuum was held for 1 hour to vaporise the TMCS and silanize the wafer.

Medical Grade Silicone Creates Adipose Surfaces in Silicone

To mould subsequent silicone from each master wafer, MED 6215 silicone (Nusil California, US), a medical grade silicone with permission for use in humans was used. This silicone was spun onto the wafer at 200 rpm and cured overnight in an oven at 65° C. before being peeled from the surface of the SU8 to produce both the "Original Adipose" and "Modelled Adipose" surface.

Substrate Characterisation

Fabricated implant surfaces were characterised using AFM, laser confocal imaging and Scanning Electron microscopy.

Growth of THP-1 Macrophages

Human THP-1 monocyte cells were cultured in RPMI 1640 medium, "normal media" (Sigma Aldrich, UK) supplemented with 1% penicillin and streptomycin (PAA), 1% L-glutamine (PAA) and 10% Fetal Bovine Serum (PAA) in T75 tissue culture plastic (TCP) flasks (Corning Incorporated, USA). Monocytes were incubated at 37° C. in 5% $CO_2$ and media was changed weekly. THP-1 monocytes were treated with 25 nM phorbol myristate acetate (PMA, Sigma Aldrich, UK) for 24 hours to facilitate differentiation into macrophages. After differentiation, macrophages were washed twice with normal media and rested for a further 24 hrs in normal media. Prior to seeding, macrophages were serum starved for 24 hrs in 0.5% FBS media to synchronise these cells. Cells were seeded at 250,000 cells per well of a 24 well culture plate (Corning Incorporated, USA) and each experiment was performed in triplicate.

Preparation of Culture Surfaces

Manufactured surfaces were cut into 15 mm disks using a punch cutter, before being adhered to the bottom of a 24 well plate (Corning Incorporated) using a drop of uncured MED 6215 silicone, which was cured overnight at 65° C. TCP and a smooth MED6215 silicone surface, manufactured by curing PDMS on a plain silicon wafer were used as controls. Prior to cell seeding manufactured surfaces were washed twice with PBS and sterilised using 70% ethanol for 15 minutes. Manufactured implants were air dried for half an hour and washed twice with PBS. For Confocal microscopy, 6 mm biopsies were taken of the manufactured surfaces and RNA Extraction, cDNA Synthesis and Quantitative Real Time Polymerase Chain Reaction Cells were washed once with PBS, before being lysed in buffer RLT (Qiagen, UK) and the lysate collected. RNA was extracted using the Qiagen RNA Mini kit as per manufacturer's instructions. RNA purity and quantity was assessed using a NanoDrop 2000c spectrophotometer (Thermo Scientific, USA) before RNA was transcribed to cDNA using a qScripts cDNA synthesis kit (Quanta Biosciences, USA). qRT-PCR was performed on a LightCycler 480 machine (Roche Diagnostics, Germany) as described previously(20). The gene expression of Tumour Necrosis Factor Alpha (TNF alpha), Interleukin Beta1 (ILB1), Interleukin 6 (IL6), Interleukin 10 (IL10) and Mannose Receptor (CD206) were analysed. Primers and probes were designed using the Universal Probe Library and purchased from Sigma Aldrich, UK. ΔCT values were calculated by subtracting CT values from the averaged reference gene Beta Actin. Relative gene expressions were calculated using the ΔΔCT method.

Inflammatory Marker Cytokine Array

Cell culture media was aspirated from the cell culture well at each time point and stored at −80° C. until further use. Luminex analysis was performed by ProcartPlex™ Multiplex Immunoassay (eBioscience, Vienna, Austria) for human IL-1RA, IL-1beta, IL-6, IL-8, IL-10, IL-12, TNF alpha, IFN gamma and GRO alpha as per manufactures instructions.

Immunocytochemistry

Immunocytochemistry was performed on breast derived fibroblasts for vinculin, F-Actin and DAPI. Immunocytochemistry was performed on macrophages using Integrin α-v. Disks of the manufactured implant surfaces were cut with a 6 mm punch biopsy, adhered to 8 mm circular cover-slips using 3 μl of mixed MED-6215 silicone and cured at 65° C. overnight, sterilising and seeding with 10,000 macrophages or 5,000 fibroblasts.

After 24 hours of cell growth, cells were fixed in 10% neutral buffered formalin (Sigma-Aldrich, UK) for 1 hr, washed in a Tris Buffered Saline (TBS, Sigma-Aldrich, UK) and unreacted formalin was quenched by incubating in 1% glycine for 30 minutes. Fixed cells were permeabilised with 1% Triton-X 100 (Sigma-Aldrich, UK) for 30 minutes. Cells were then washed twice before blocking in 10% Bovine Serum Albumin (BSA, Sigma-Aldrich, UK) for 1 hr. After washing, fibroblasts were incubated in Anti-Vinculin antibody at a dilution of 1:200 in 10% BSA (V9131, Sigma-Aldrich, UK) for 1 hr at room temperature (RT). After washing macrophages were incubated in Anti-Integrin α-v at a dilution of 1:750 in 10% BSA (ab124968, Abcam, Cambridge, UK) for 1 hr at RT. Cells were washed in TBS-Tween (TBST, 0.1% Tween in TBS) and incubated in the secondary antibody, anti-mouse (anti-rabbit) Alexa-Fluor-488 dye (Invitrogen, UK) at a 1:200 concentration for 1 hr at RT in the dark. Cells were washed with TBST, incubated with Rhodamine Phalloidin (Sigma-Aldrich, UK) at a concentration of 1:1000 for 45 minutes, with 4',6-diamidino-2-phenylindole (DAPI, 1:500 in TBST, Invitrogen, UK) for 15 minutes before they were washed twice and placed in PBS at 4° C. until imaging.

Confocal Microscopy

Images were acquired using a Leica SP5 (Leica, Wetzlar, Germany) inverted laser-scanning confocal microscope with an ×40 immersion lens. Samples were imaged in PBS and ImageJ was used to compile z-stack slices using the maximum projection tool.

Scanning Electron Microscopy

Growth media was removed and cells were washed twice with 0.1 M hepes buffer (Formedium, UK). Cells were fixed in 2.5% glutaraldehyde (Sigma-Aldrich) and 0.1M hepes buffer (Formedium, UK) for 1 hr at RT. Following two wash steps in distilled water of 15 minutes each, the tissue was dehydrated through a graded series of ethanol, 25%, 50%, 75%, 90%, and 100%, for 15 minutes at each step. Three further washes in 100% ethanol were then performed before the cells and implant were critical point dried (Quorum Technologies Ltd. East Sussex, England).

Results

Adipose Surface Remains Intact after Tissue Fixation

Figure 2:
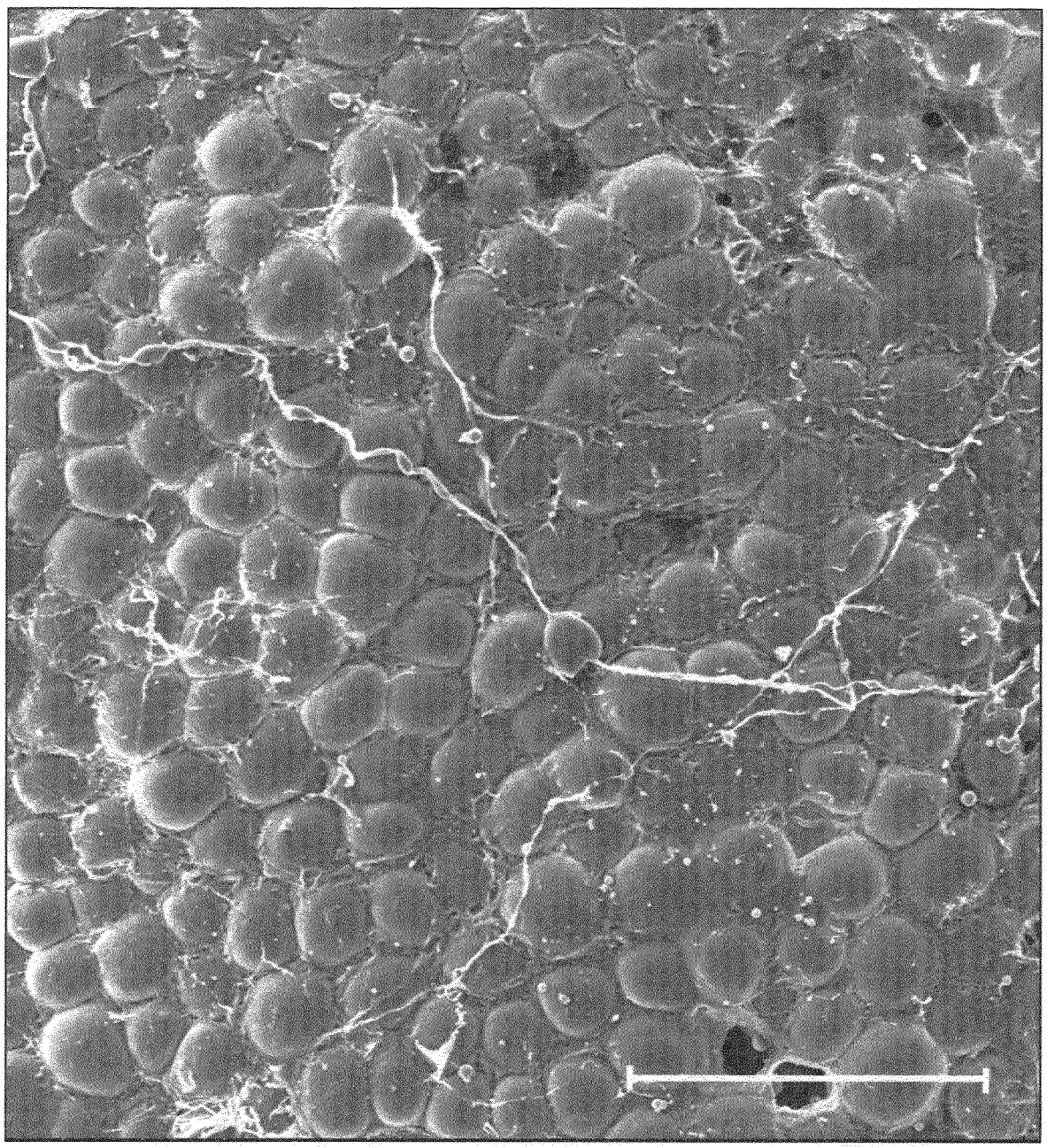
FIG. 2 shows S.E.M. image of surface of breast locule illustrating the close-packed spherical nature of this surface. Scale bar 100 µm.

Breast adipose tissue texture was demonstrated to be retained after tissue fixation. S.E.M. images illustrate the texture on the surface of these breast locules; a close packed arrangement of spheres with a variable layer of fibres running over their surface (FIG. 2).

Laser Confocal Microscopy Defines Adipose Locule Texture Statistics

Laser confocal imaging (FIG. 3) shows that the natural surface in the breast was imaged successfully by the laser confocal microscope. The adipocytes present, the individual building blocks of this surface, also retained their spherical nature and had not collapsed which demonstrates that the fixation technique had successfully preserved the structural content of these spheres.

Figure 4:
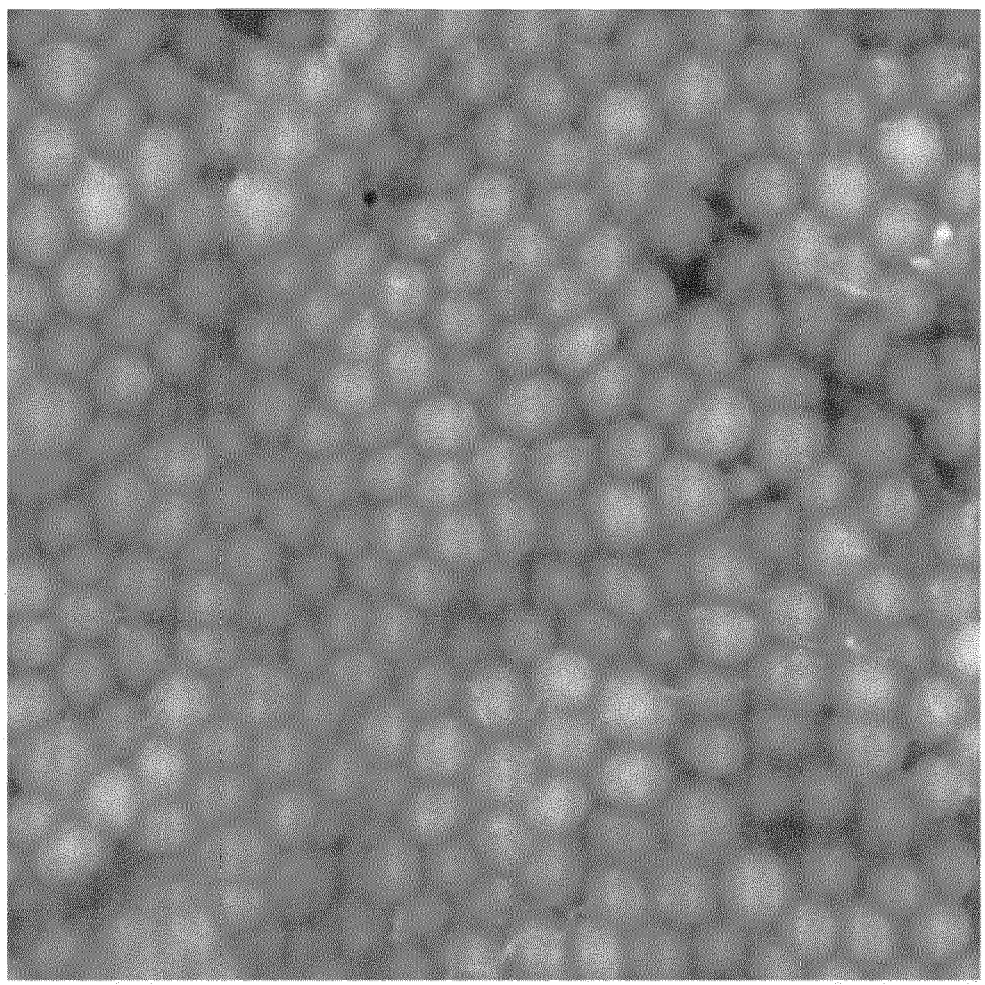
FIG. 4 shows laser confocal output capturing the "Adipose Original Surface".

A bitmap of the surface measurement data, where height was represented as 256 grayscales was extracted from the laser confocal images (FIG. 4). This defined the "Original Adipose" surface.

Laser Confocal Data Allows Extraction of Statistical Data from the Adipose Surface Matlab code, written to extract the statistical data of the surface allowed measurement of nearest neighbour distances and sphere diameters (FIG. 5).

Figure 6B:
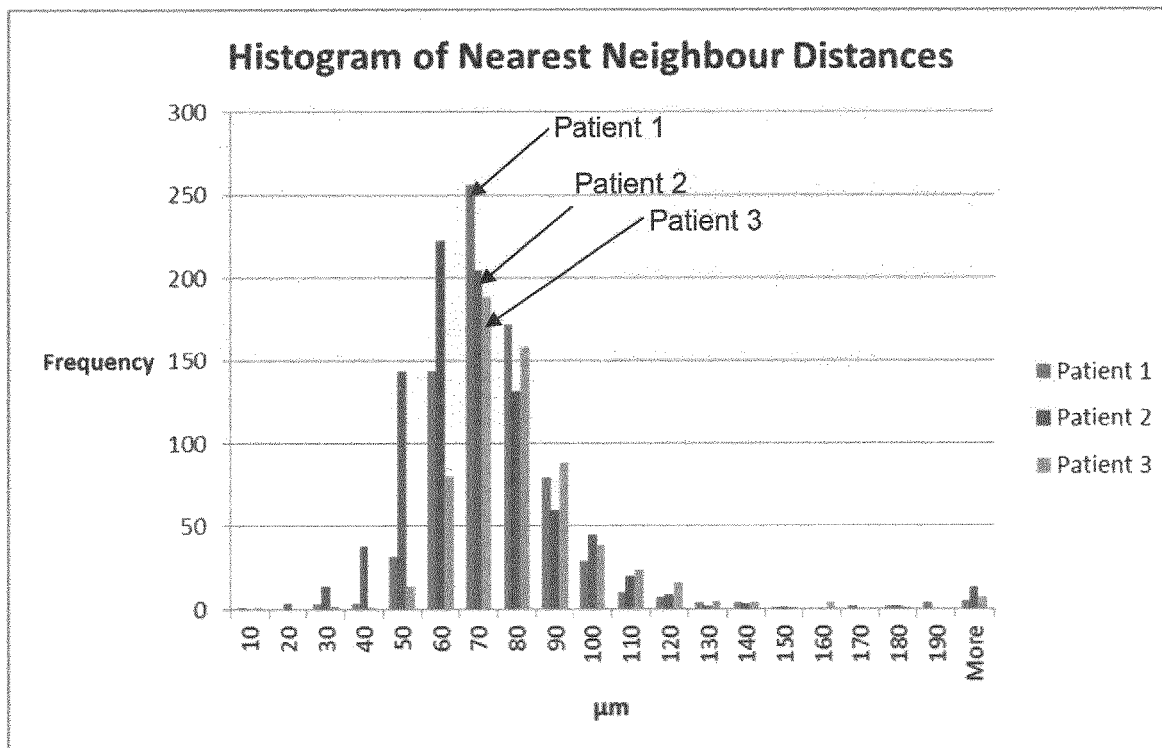
FIG. 6B is a histogram of Nearest Neighbour Distances.

Sphere diameters ranged from 16.8 μm to 152.53 μm (mean 43.26 μm, median 40.6 μm, S.D. 13.69 μm) (FIG. 6A), whilst nearest neighbour distances ranged from 30.69 μm to 159.09 μm (mean 71.4 μm, median 66.8 μm, S.D. 31.77 μm) (FIG. 6B).

Matlab Code Defines the Base Structure of the "Adipose Surface"

Based upon the recognised spheres on the surface of a sample, Matlab code generated the base texture of the new grayscale Modelled Adipose surface based upon the position and sphere diameters on this surface (FIGS. 6C, 7).

AFM Statistically Quantifies the Adipose Surface

Height profiles of 12 adipocytes from data were obtained from the AFM scans of the adipocyte surfaces. Height profiles varied between each adipocyte, but the information gained allowed a an etch recipe to be determined to mimic the height profiles/texture on the modelled adipose surface.

AFM scans of this nano-texture showed it has a random roughness on its surface and a height profile which matches that of the adipocytes.

The surface of the SU-8 mould was textured using a 6.5 minute oxygen etch recipe which produced a texture on the surface of the mould (FIG. 12B, etched for 6.5 mins) with statistics and a surface height which lay within the range of that measured in native breast adipocytes.

Figure 10:
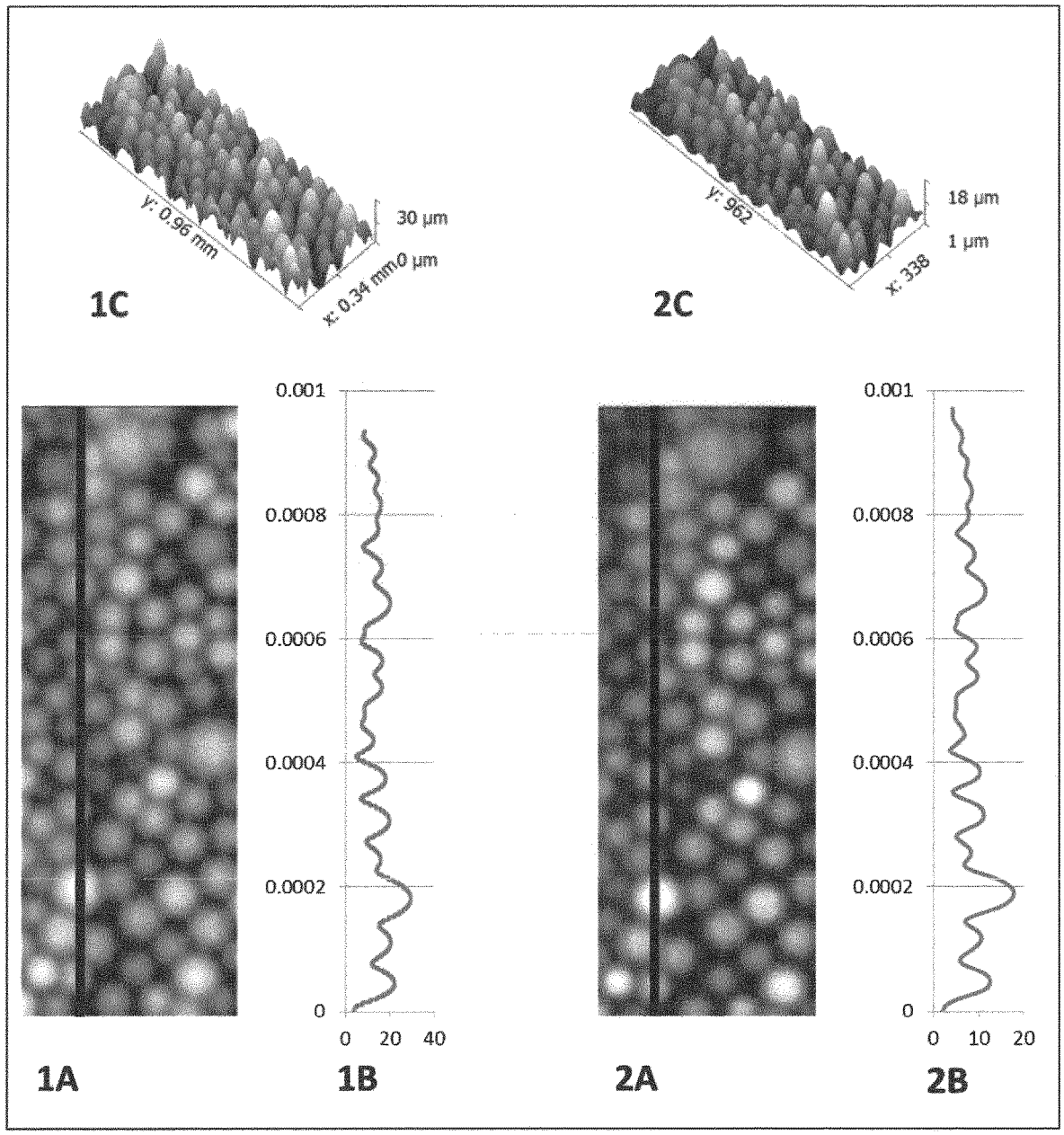
FIG. 10 shows information on the native tissue and on the Modelled Surface when transferred into Silicone: 1A bitmap image height data generated from Matlab programme; 1B height profile of bitmap 1A along the black line in 1A; 10, a 3D representation of the bitmap in 1A; 2A a 2D scan of the actual silicone surface created using SU8 and scanned with a laser confocal microscope; 2B height profile of 2A along the black line in this figure; and 2C a 3D representation of the actual modelled surface Actual Laser confocal scanned surface.

Laser Confocal Measurement Demonstrates Successful Transfer of the Modelled Adipose Surface into Silicone FIG. 10-1A illustrates the height data generated by the Matlab code for the surface of the modelled adipose surface in 2d, as a 3D representation (10-1C) and as a graph of the profile of this surface (10-1B) along the black line in image 10-1A. FIG. 10 2A, 2B, 2C shows the adipose modelled surface scanned using a laser confocal microscope and the same 2D, 3D and profile results.

Growth of Human Derived Fibroblasts and Macrophages Shows Recognition of Surface Macro-Texture Fibroblasts and macrophages were grown in culture on the surface of the Original Adipose and Modelled Adipose Surfaces. Fibroblasts adhered to these surfaces and conformed to the macro texture beneath them, orientating along the valleys of the spherical features beneath them as shown most apparently in FIG. 11A, 12A.

Figures 11A, 11B:
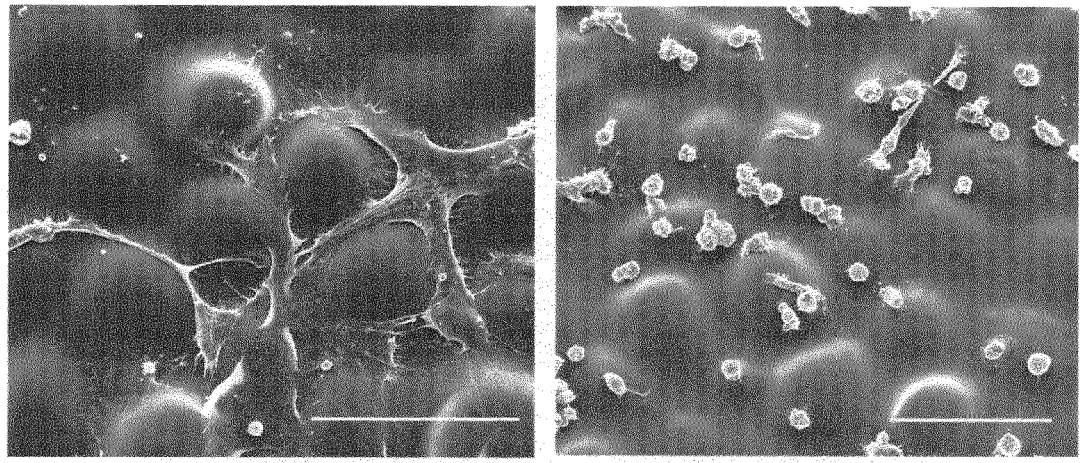
FIGS. 11A and 11B show an S.E.M. image of Fibroblasts adhered to Adipose surface and S.E.M. image of THP-1 Macrophages attached to Adipose Surface.
Figures 12A, 12B:
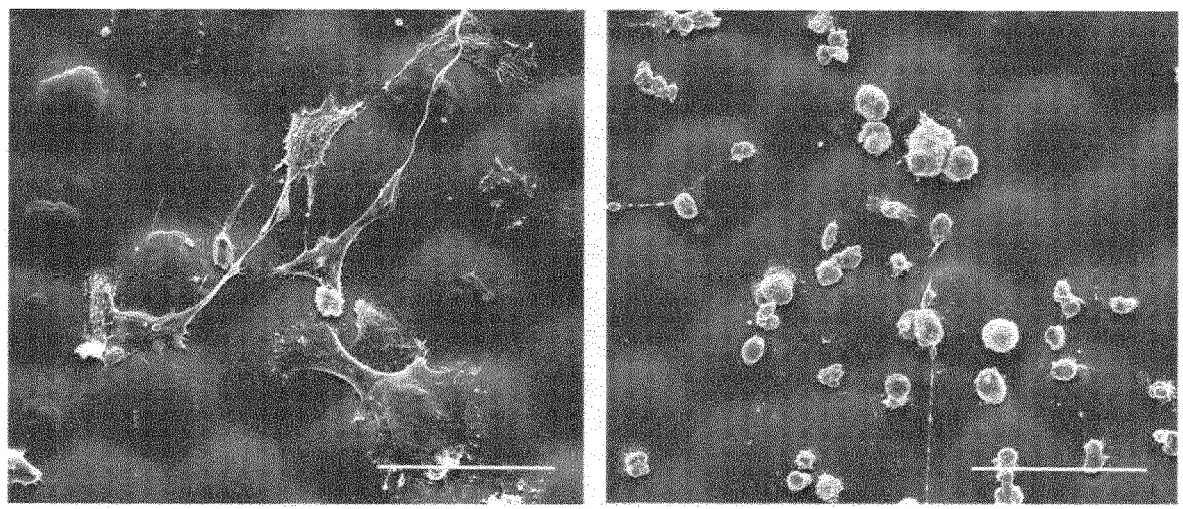
FIGS. 12A and 12B show an S.E.M. image of Fibroblasts adhered to Modelled surface and S.E.M. image of THP-1 Macrophages attached to Modelled Surface.

Macrophages were also clustered around the circumference of the spherical features in FIG. 11B, 12B.

No significant differences in the focal adhesion complexes was noted between the Original Adipose and Modelled Adipose Surfaces in both fibroblasts and macrophages.

Figure 13:
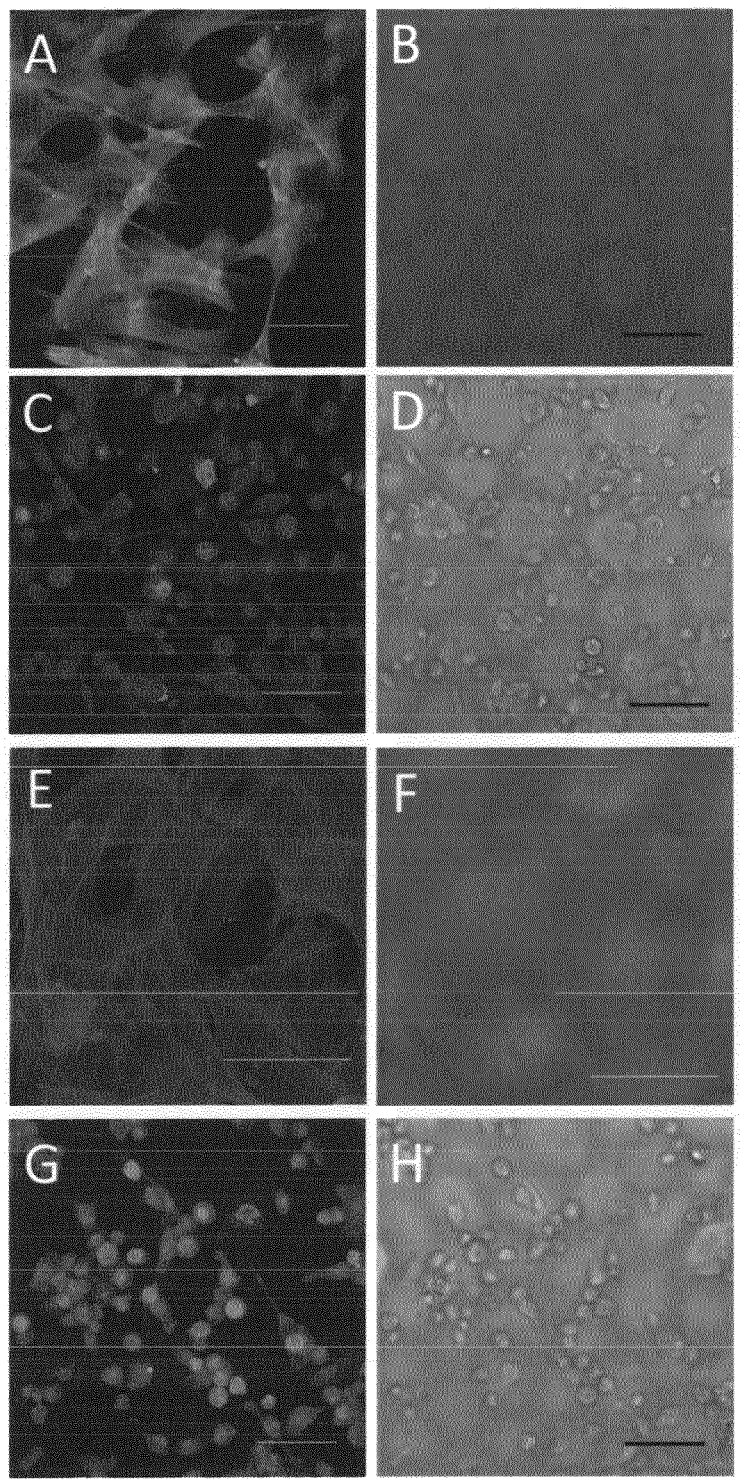
FIGS. 13A, 13C, 13E and 13G are Fibroblasts and Macrophages adhered to surfaces shown on FIGS. 13B, 13D, 13F and 13H (Blue=Nuclei, Green=Focal Adhesions, Red=Cytoskeleton).

However the pattern of macro-texture recognition and growth of fibroblasts around the periphery of the spherical shapes beneath them was continuous in the images shown in FIGS. 13A and 13E.

Figure 14:
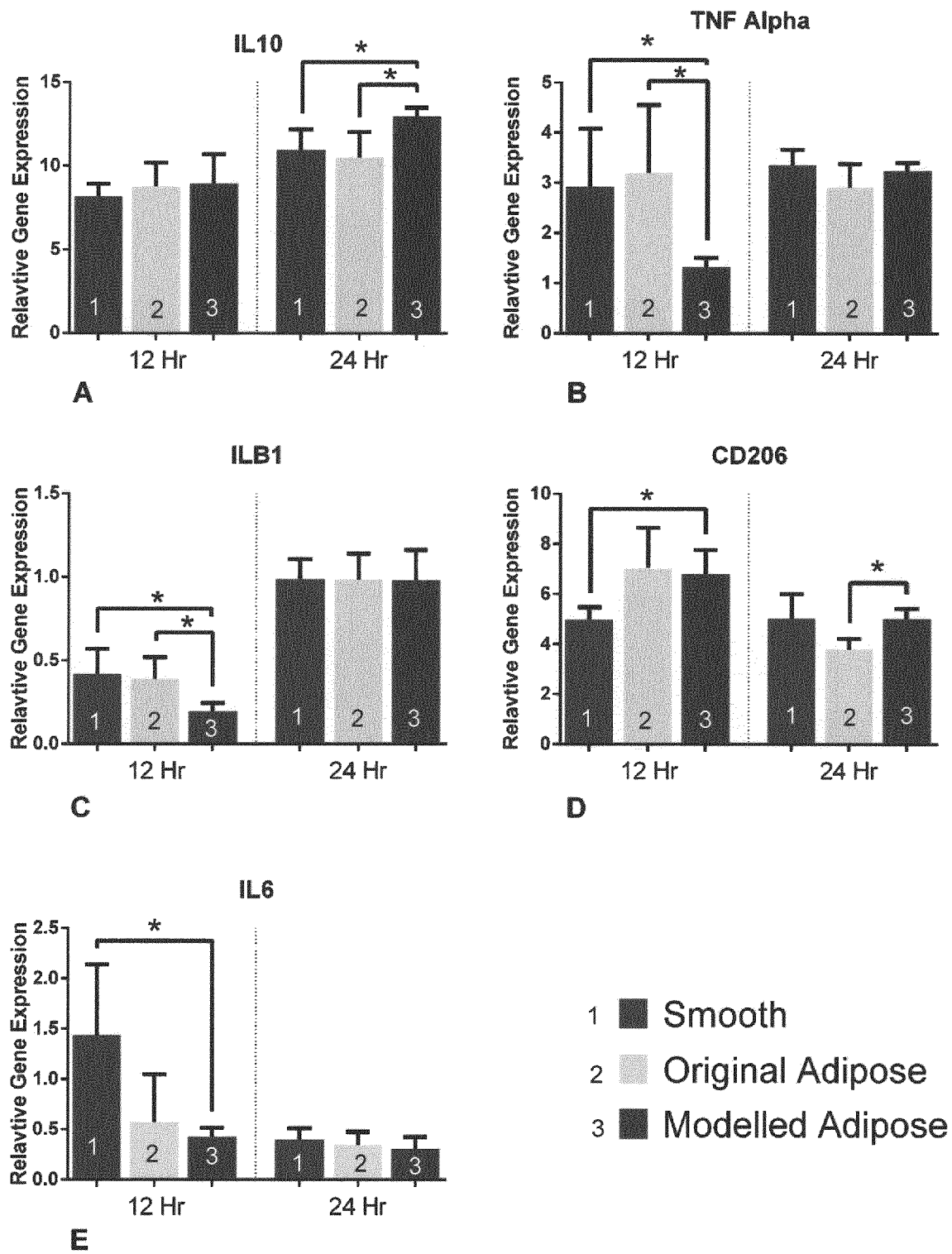
FIG. 14 shows QRT-PCR Relative gene expressions of IL-10, TNF-Alpha, ILB1, CD206 and IL6 compared to Tissue Culture Plastic.

Modelled Adipose Surface Induces a Positive Alteration in Gene Profiles Cultured on its Surface when Compared to Smooth Silicone Surfaces As shown by FIG. 14, the Modelled adipose surface provoked a pro-M2 polarization in THP-1 macrophages. At 12 hours TNF alpha (vs original adipose p=0.0008, vs smooth p=0.0008), ILB1 (vs original adipose p=0.0007, vs smooth p=0.0006) and IL6 (vs smooth p=0.0006) had the lowest relative gene expression in the modelled surface compared to the smooth and Original Adipose Surface. At 24 hours IL10 which is an anti-inflammatory cytokine had the highest expression in the modelled adipose surface compared to the Original Adipose surface (p=0.0003) and the smooth surface (p=0.0003). CD206, which is a marker of M2a phenotype had a higher relative expression in the Modelled Adipose surface when compared to the smooth surface at 12 hours (p=0.0001) and a higher than Original Adipose surface (p<0.0001).

It can also be seen that in many cases, the manufactured surfaces had less inflammatory influence on THP-1 macrophages than tissue culture plastic itself.

Figure 15:
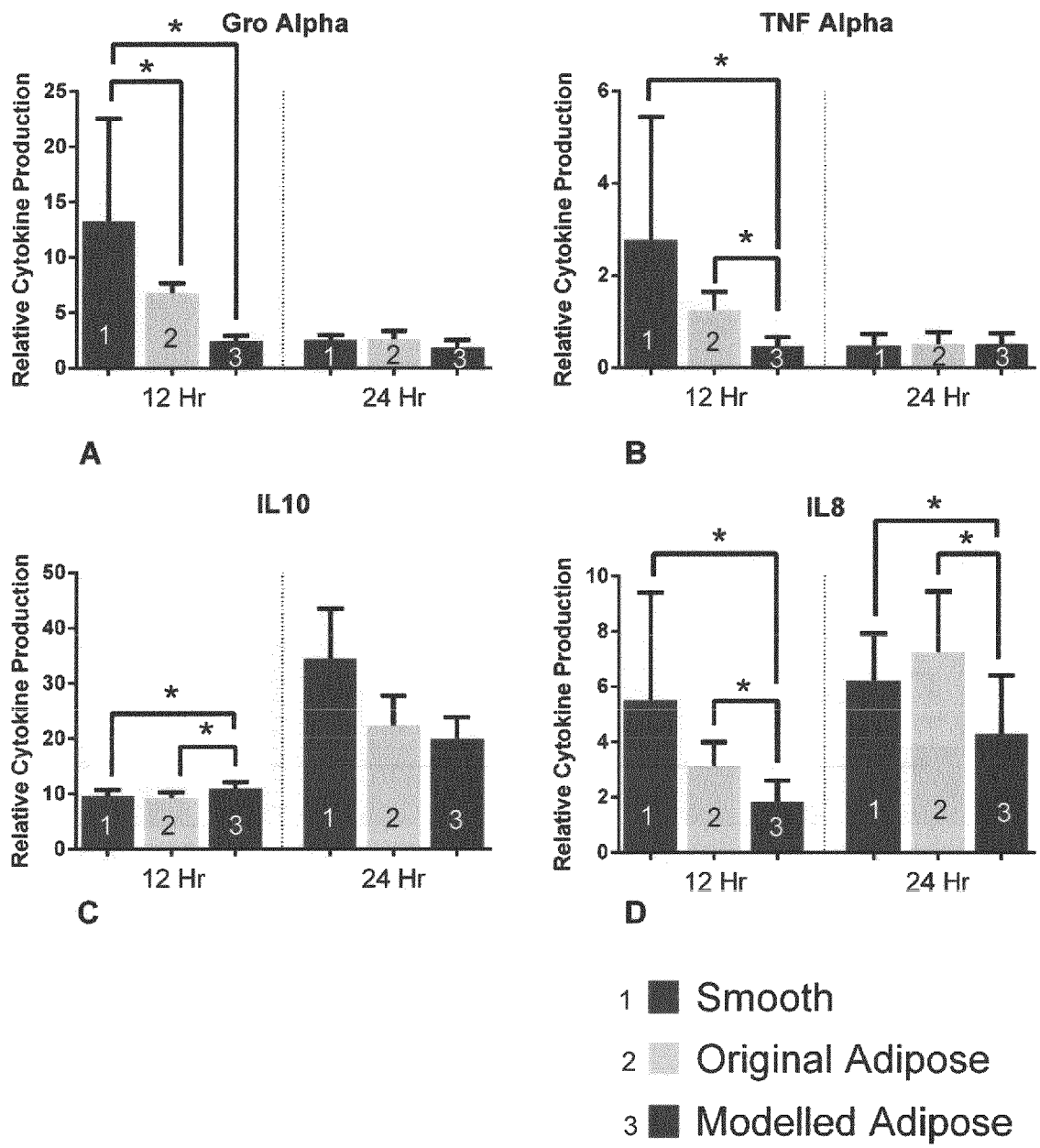
FIG. 15 shows Relative cytokine production of GRO-Alpha, IL10, IL8 and TNF Alpha in comparison to Tissue Culture Plastic.

Modelled Adipose Surface Induces a Positive Alteration in Cytokine Expression in Macrophages Cultured on its Surface Cytokine profiles of the same macrophages analysed in the PCR data above, reinforced the fact that the Modelled Adipose Surface provoked a positive effect on THP-1 Macrophages (FIG. 15). At 12 hours, the Modelled Adipose Surface provoked the highest production of anti-inflammatory cytokine IL10 (vs Original Adipose p=0.0032 and vs smooth p=0.0186) and the lowest production of anti-inflammatory Gro-Alpha (vs Original Adipose p=0.0031 and vs smooth p=0.0192), TNF-Alpha (vs Original Adipose p<0.0001 and vs smooth p=0.0186), neutrophil chemoattractant IL8 (vs Original Adipose p=0.0035 and vs smooth p=0.0134). At 24 Hours IL8 levels again showed lowest levels in the Modelled Adipose Surface (vs Original Adipose p=0.0098 and vs smooth p=0.0477).

Observations

The novel surface texture has been shown to reduce the inflammatory response of macrophages and induce an alternatively activated macrophage phenotype in the initial biomaterial in-vitro response.

Via careful surface analysis and subsequent modelling, the inventors have characterised the relevant features of native breast adipose tissue. Specifically, this has led to a better understanding of the shapes and arrangement of features on the surface of native breast tissue and this in turn has assisted replication of these features in silicone. By combining a photolithographic technique and oxygen plasma etching, usually reserved for the microelectronics industry, a complex overlaid micro- and nano-texture has been achieved in the surface of medical grade silicone, which mimics that found within the breast.

To examine the in-vitro effect of implant texture a challenging macrophage-based assay has been used, being a cell type with an undisputed role in the regulation of the foreign body reaction.(25) Macrophages arrive at the biomaterial wound interface within the first few hours and remain for several days and dictate the downstream foreign body reaction, which is why 12 and 24 hr time points have been chosen to assess their reactions.(26) Pro-inflammatory cytokines IL-1β, (27), IL-6(28), TNF alpha(29) and IL-8(30) involved in macrophage activation and IL-10(31) a potent anti-inflammatory cytokine all have important roles in the reaction of macrophages to biomaterial surfaces and in dictating the remainder of the foreign body reaction.(31) IL8 and TNF-Alpha have also been found to be upregulated in contracted fibrotic capsules.(32) Each of the genes associated with these cytokines or the cytokines themselves were favourably modulated by the novel implant surface.

Fibroblasts are the traditional cell type used to assess the reaction to implant surfaces as they generate extra cellular matrix which is the main component of the capsule. Fibroblasts were included in the assessment of the implant surfaces as an indicator of cell alignment because this, with the smooth surface implants, has been theorised to increase contracture rates.(17) Fibroblasts are recruited from approximately 24-48 hours after the wound is created at the end of the inflammatory phase and at the beginning of the proliferative phase and are activated by the chemoattractants and cytokines produced by macrophages.(33) The implant surface has shown that the fibroblasts recognise the surface of the implant and track along the valleys between each hemisphere on the surface in a range of different directions, thus breaking the alignment seen in the smooth surface implants.

Our results show that two different cell types are influenced by surface topography and that the modulation of this response is possible by providing a topography that mimics an adipose tissue surface, this response being independent of implant chemistry.(34)

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

REFERENCES

1. Cash T F, Duel L A, Perkins L L, Sarwer D B. Women's psychosocial outcomes of breast augmentation with silicone gel-filled implants: A 2-year prospective study. Plastic and reconstructive surgery. 2002; 109(6):2122-3.
2. The International Society of Aesthetic Plastic Surgery Releases Statistics on Cosmetic Procedures Worldwide [press release]. 2014.
3. Gabriel S E, Woods J E, O'Fallon W M, Beard C M, Kurland L T, Melton L J. Complications Leading to Surgery after Breast Implantation. The New England journal of medicine. 1997; 336(10):677-82.
4. Anderson J M. BIOLOGICAL RESPONSES TO MATERIALS. Annual Review of Materials Research. 2001; 31(1):81-110.
5. Collis N, Sharpe D T. Recurrence of subglandular breast implant capsular contracture: Anterior versus total capsulectomy. Plastic and reconstructive surgery. 2000; 106(4):792-7.
6. Araco A, Caruso R, Araco F, Overton J, Gravante G. Capsular contractures: a systematic review. Plast Reconstr Surg. 2009; 124(6):1808-19.
7. De Nicola R R. Permanent artificial (silicone) urethra. J Urol. 1950; 63:168-72.
8. Ashley F L. A new type of breast prosthesis. Preliminary report. Plastic and reconstructive surgery. 1970; 45(5): 421-4.

9. Batich C, Williams J, King R. Toxic hydrolysis product form a biodegradable foam implant. Journal of Biomedical Materials Research. 1989; 23(SUPPL. A3):311-9.
10. Gasperoni C, Salgarello M, Gargani G. Polyurethane-covered mammary implants: A 12-year experience. Annals of Plastic Surgery. 1992; 29(4):303-8.
11. Barr S, Bayat A. Breast implant surface development: perspectives on development and manufacture. Aesthetic surgery journal/the American Society for Aesthetic Plastic surgery. 2011; 31(1):56-67.
12. Barnsley G P, Sigurdson L J, Barnsley S E. Textured surface breast implants in the prevention of capsular contracture among breast augmentation patients: A meta-analysis of randomized controlled trials. Plastic and reconstructive surgery. 2006; 117(7):2182-90.
13. Wong C H, Samuel M, Tan B K, Song C. Capsular contracture in subglandular breast augmentation with textured versus smooth breast implants: A systematic review. Plastic and reconstructive surgery. 2006; 118(5): 1224-36.
14. Bettinger C J, Langer R, Borenstein J T. Engineering substrate topography at the Micro- and nanoscale to control cell function. Angewandte Chemie—International Edition. 2009; 48(30):5406-15.
15. Hynes R O. The extracellular matrix: Not just pretty fibrils. Science. 2009; 326(5957):1216-9.
16. Dvir T, Timko B P, Kohane D S, Langer R. Nanotechnological strategies for engineering complex tissues. Nat Nano. 2011; 6(1):13-22.
17. Brandt B, Breiting V, Christensen L. Five years experience of breast augmentation using silicone gel prostheses with emphasis on capsule shrinkage. Scandinavian Journal of Plastic and Reconstructive Surgery. 1984; 18(3): 311-6.
18. Del Rosario A D, Bui H X, Petrocine S, Sheehan C, Pastore J, Singh J, et al. True synovial metaplasia of breast implant capsules: A light and electron microscopic study. Ultrastructural Pathology. 1995; 19(2):83-93.
19. Rasband W S. ImageJ 1997-2012. Available from: http://imagej.nih.gov/ij/.
20. Syed F, Ahmadi E, Iqbal S A, Singh S, McGrouther D A, Bayat A. Fibroblasts from the growing margin of keloid scars produce higher levels of collagen i and III compared with intralesional and extralesional sites: Clinical implications for lesional site-directed therapy. British Journal of Dermatology. 2011; 164(1):83-96.
25. Kenneth Ward W. A Review of the Foreign-body Response to Subcutaneously-implanted Devices: The Role of Macrophages and Cytokines in Biofouling and Fibrosis. Journal of diabetes science and technology (Online). 2008; 2(5):768-77.
26. Gerullis H, Georgas E, Bor, # xf3, s M, Klosterhalfen B, et al. Inflammatory Reaction as Determinant of Foreign Body Reaction Is an Early and Susceptible Event after Mesh
Implantation. BioMed Research International. 2014; 2014:6.
27. Collie A M B, Bota P C S, Johns R E, Maier R V, Stayton P S. Differential monocyte/macrophage interleukin-1β production due to biomaterial topography requires the β2 integrin signaling pathway. Journal of Biomedical Materials Research Part A. 2011; 96A(1):162-9.
28. Kossovsky N, Freiman C J, Stassi J B, Mena E. Cytokine Expression in Response to Biomaterials. ImmunoMethods. 1993; 3(1):43-9.
29. Ma N, Petit A, Yahia L, Huk O L, Tabrizian M. Cytotoxic reaction and TNF-alpha response of macrophages to polyurethane particles. Journal of biomaterials science Polymer edition. 2002; 13(3):257-72.
30. Brodbeck W G, Nakayama Y, Matsuda T, Colton E, Ziats N P, Anderson J M. BIOMATERIAL SURFACE CHEMISTRY DICTATES ADHERENT MONOCYTE/MACROPHAGE CYTOKINE EXPRESSION IN VITRO. Cytokine. 2002; 18(6):311-9.
31. Jones J A, Chang D T, Meyerson H, Colton E, Kwon I K, Matsuda T, et al. Proteomic analysis and quantification of cytokines and chemokines from biomaterial surface-adherent macrophages and foreign body giant cells. Journal of Biomedical Materials Research Part A. 2007; 83A(3):585-96.
32. Kyle D J T, Harvey A G, Shih B, Tan K T, Chaudhry I H, Bayat A. Identification of molecular phenotypic descriptors of breast capsular contracture formation using informatics analysis of the whole genome transcriptome. Wound Repair and Regeneration. 2013; 21(5):762-9.
33. Bainbridge P.1 BBC. Wound healing and the role of fibroblasts. Journal of Wound Care. 2013; 22(8):407-12.
34. Chen S, Jones J A, Xu Y, Low H Y, Anderson J M, Leong K W. Characterization of topographical effects on macrophage behavior in a foreign body response model. Biomaterials. 2010; 31(13):3479-91.

The invention claimed is:

1. An implant material having an implant surface, which implant surface comprises a plurality of tissue-contacting members arranged in a regular or irregular two-dimensional array, each tissue-contacting member having a convex curved tissue-contacting surface, wherein the implant surface has 1000 to 50000 tissue-contacting members per cm$^2$, and wherein an average height of the plurality of tissue-contacting members is from 5 μm to 90 μm.

2. An implant material according to claim 1, wherein substantially all of the implant surface is provided by the convex curved tissue-contacting surfaces of the tissue-contacting members.

3. An implant material according to claim 1, wherein the convex curved tissue-contacting surface has spherical curvature.

4. An implant material according to claim 1, wherein the plurality of tissue-contacting members is a plurality of truncated hemispheres arranged to form a two-dimensional array of fused hemispheres.

5. An implant material according to claim 1, wherein the plurality of tissue-contacting members include tissue-contacting members of different heights such that there is height variation within the population of tissue-contacting members.

6. An implant material according to claim 1, wherein the mean average diameter of the plurality of tissue-contacting members is from 1 μm to 120 μm.

7. An implant material according to claim 1, wherein the mean average centre-to-centre nearest neighbour spacing of the array of tissue-contacting members is from 1 μm to 120 μm.

8. A synthetic implant material according to claim 1, wherein the tissue-contacting surface of each tissue-contacting member comprises an organosilicon polymer.

9. A synthetic implant material according to claim 1, wherein the tissue-contacting surface of each tissue-contacting member comprises polydimethylsiloxane.

10. A synthetic implant material according to claim 1, wherein the implant material forms at least part of the surface layer of a breast implant.

11. A template for use in preparing an implant material according to claim 1, said template having a textured surface corresponding to the implant surface, or a negative of the implant surface.

12. A method of preparing an implant material having an implant surface comprising the steps of acquiring three-dimensional spatial data from an adipose tissue surface, processing the spatial data, and using the processed spatial data to create the implant surface of the implant material, wherein the implant surface comprises 1000 to 50000 tissue-contacting members per cm$^2$, each tissue-contacting member having a convex curved tissue-contacting surface that mimics the adipose tissue surface.

13. A method according to claim 12, wherein using the processed spatial data includes making a template embodying the processed spatial data and using said template to make the implant surface of the implant material.

14. An implant material comprising an implant surface as prepared by a method according to claim 12.

15. A template for use in preparing an implant material according to claim 14, said template having a textured surface corresponding to the implant surface, or a negative of said implant surface.

16. A method of making a textured implant material comprising using the template of claim 15.

17. A method of implanting into the human body an implant comprising the implant material according to claim 1.

18. A method, comprising the step of implanting into a human body a breast implant comprising the implant material according to claim 1.

19. An implant material having an implant surface, which implant surface comprises a plurality of tissue-contacting members arranged in a regular or irregular two-dimensional array, each tissue-contacting member having a convex curved tissue-contacting surface, wherein the implant surface has 10000 to 40000 tissue-contacting members per cm$^2$, and wherein the plurality of tissue-contacting members has an average height of 5 μm to 90 μm.

* * * * *